US007253182B2

(12) United States Patent
Noe et al.

(10) Patent No.: US 7,253,182 B2

(45) **Date of Patent: *Aug. 7, 2007**

(54) ENANTIOMERICALLY PURE BASIC ARYLCYCLOALKYLHYDROXYCARBOXYLIC ESTERS, PROCESSES FOR THEIR PREPARATION AND THEIR USE IN MEDICAMENTS

(75) Inventors: Christian Noe, Frankfurt am Main (DE); Ernst Mutschler, Mainz (DE); Günter Lambrecht, Mainz (DE); Michael Elgert, deceased, late of Frankfurt am Main (DE); by Ruth Irene Elgert, legal representative, Frankfurt am Main (DE); Sittah Czeche, Gotha (DE); Magali Waelbroeck, Brussels (BE)

(73) Assignee: Sofotec GmbH & Co. KG, Frankfurt (DE)

( * ) Notice: Subject to any disclaimer, the term of this patent is extended or adjusted under 35 U.S.C. 154(b) by 672 days.

This patent is subject to a terminal disclaimer.

(21) Appl. No.: 10/601,542

(22) Filed: Jun. 23, 2003

(65) Prior Publication Data

US 2003/0220400 A1 Nov. 27, 2003

Related U.S. Application Data

(60) Division of application No. 09/901,217, filed on Jul. 9, 2001, now Pat. No. 6,613,795, which is a continuation-in-part of application No. 09/309,960, filed on May 11, 1999, now Pat. No. 6,307,060.

(51) Int. Cl.
*A61K 31/44* (2006.01)

(52) U.S. Cl. .................................................... 514/306

(58) Field of Classification Search ................. 514/306
See application file for complete search history.

(56) References Cited

U.S. PATENT DOCUMENTS

| | | | | |
|---|---|---|---|---|
| 2,882,276 A | | 4/1959 | Lunsford, I | |
| 2,956,062 A | * | 10/1960 | Lunsford | 548/556 |
| 2,980,693 A | | 4/1961 | Cavalla et al. | |
| 3,157,671 A | | 11/1964 | Bowman, II et al. | |
| 3,185,702 A | | 5/1965 | Lunsford, III | |
| 3,691,198 A | | 9/1972 | Brown et al. | |
| 4,208,423 A | | 6/1980 | Pfister I | |
| 4,228,171 A | | 10/1980 | Pfister II | |
| 4,353,922 A | * | 10/1982 | Pfister | 514/339 |
| 6,063,808 A | | 5/2000 | Fabiano et al. | |

FOREIGN PATENT DOCUMENTS

| | | |
|---|---|---|
| AU | 233794 | 10/1959 |
| CA | 625276 | 8/1961 |
| CA | 629039 | 10/1961 |
| GB | 821436 | 10/1959 |
| GB | 855430 | 11/1960 |
| GB | 1170831 | 11/1969 |
| NL | 99 767 | 11/1961 |
| WO | WO 98/00016 | 1/1998 |
| WO | WO 98/00109 | 1/1998 |
| WO | WO 98/00132 | 1/1998 |
| WO | WO 98/00133 | 1/1998 |
| WO | WO 98/21183 | 5/1998 |

OTHER PUBLICATIONS

Iulia Demian et al.: High-Performance Liquid Chromatographic Separation of 3-[(Cyclopentylhydroxiphenylacetyl]-1, 1-Dimethylpyrrolidinium Bromide Diastereomers, Journal of Liquid Chromatography, 13(4), 779-787 (1990).

Chemical Abstracts 119: 108934x.

Chemical Abstracts 123: 47690y.

Zhi Wang et al.: "Use of Cyclodexttrin as Chiral Selector for the Chiral Separation of Anticholinergic Drugs such as Anisodamine and Glycopyrronium in Capillary Zone Electrophoresis", J. High Resol. Chromatogr., vol. 19, Dec. 1996, pp. 697-699.

* cited by examiner

*Primary Examiner*—San-Ming Hui
(74) *Attorney, Agent, or Firm*—Laurence A. Greenberg; Werner H. Stemer; Ralph E. Locher

(57) ABSTRACT

Disclosed are enantiomerically pure cyclic aminoalcohol esters of arylcycloalkylhydroxycarboxylic acids with at least 90% enantiomeric excess of the (3R,2'R), (3S,2'R), (3R,2'S), or (3S,2'S) configured enantiomer.

36 Claims, No Drawings

ENANTIOMERICALLY PURE BASIC ARYLCYCLOALKYLHYDROXYCARBOXYLIC ESTERS, PROCESSES FOR THEIR PREPARATION AND THEIR USE IN MEDICAMENTS

CROSS REFERENCE TO RELATED APPLICATION

This divisional application claims the benefit under 35 U.S.C. §120 of U.S. application Ser. No. 09/901,217, filed Jul. 9, 2001 now U.S. Pat. No. 6,613,795, which was a continuation-in-part of application Ser. No. 09/309,960, filed on May 11, 1999, now U.S. Pat. No. 6,307,060.

BACKGROUND OF THE INVENTION

Field of the Invention

The present invention provides certain enantiomerically pure aminoalcohol esters of arylcycloalkylhydroxycarboxylic acids, and processes for their preparation and medicinal use.

Esters of arylcycloalkylhydroxy acids with cyclic alcohols containing a quaternary nitrogen represented by formula I (1)

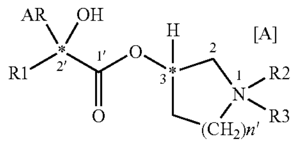

comprising a hydroxycarboxylic acid component in which AR is an aromatic ring and in which $R_1$ is a cycloaliphatic ring, and comprising an alcohol component in which the hydroxyl group is located on a dimethylpyrrolidinium ring (n=1) or dimethylpiperidinium ring (n=2) in which $R_2$=$R_3$ is a lower alkyl and in which A is a halide, have in some instances been described as spasmolytics. If the two radicals $R_2$ and $R_3$ are identical, compounds of formula I have two chiral centers. One of the centers can be assigned to the acid moiety and relates to the position labeled 2', the second chiral center is located in the cyclic ring system at the position labeled 3. Since compounds of this structure accordingly have two chiral centers, four stereoisomers (3R,2'R; 3S,2'R; 3R,2'S and 3S,2'S) are possible in principle. To date, pure is stereoisomers of the formula I compound have been neither isolated nor synthesized, nor have they been investigated pharmacologically—which is essential for the subject matter of the present patent application. The most important representative of the formula 1, which is also used in therapy, is glycopyrronium bromide (AR=phenyl, $R_1$=cyclopentyl, $R_2$=$R_3$=methyl, n=1, A=Br). The international non-proprietary name glycopyrronium bromide refers to the racemic mixture of diastereomers, which, accordingly, contains all four stereoisomers.

The publications and patents that have hitherto been published deal either with the drug glycopyrronium bromide in the form of a mixture of stereoisomers (CAS 596-51-0), with erythro-(RN 59677-73-5) or threo-(RN 59677-70-2) configured racemates of the tertiary amino ester (CRN 131118-11-1), which can be considered as only representing an intermediate in the synthesis of the compounds of the formula 1, or with the mixture of stereoisomers of the analogous cyclohexyl derivative ($R_1$=cyclohexyl) of the formula I (where n=1) (RN 101564-29-8). The publications quoted in Chemical Abstracts 80:53209h and 80:53214f describe the results of the analyses of the crystal structures of the compounds glycopyrronium bromide and hexapyrronium bromide which are in the form of mixtures of stereoisomers. The publications quoted in Chemical Abstracts 80:66587e, 80:66588f and 89.191258 describe the results of pharmacological investigations with the mixture of stereoisomers of the compound glycopyrronium bromide, or of combination products of this substance with neostigmine and pyridostigmine. The publications quoted in Abstracts 84:43164h and 85:32832u describe the partial separation of the mixture of stereoisomers by means of a crystallization with 5-nitroisophthalic acid and the study of the threo- or erythro-configured racemates already mentioned above by NMR. Here, the authors succeeded, starting from the mixture of stereoisomers (CRN 131118-11-1), only in separating the diastereomers into the two racemates, but they did not succeed in preparing the enantiomerically pure compounds. The publications quoted in Chemical Abstracts 96:219498m, 105:48928x, 113:158782t, 89:191258k and the European Patent EP 128886 A2 describe the results of studies on the chromatographic analysis of the mixture of stereoisomers of the compound glycopyrronium bromide and the preparation of the stationary phases used. A separation of the enantiomers or an isolation of the individual stereoisomers of the formula I is not reported in any of the above-mentioned publications. In all cases mentioned, HPL-chromatographic separation succeeded only at the stage of the diastereomers. Thus, the preparation of the enantiomerically pure compounds of the formula according to the present invention is not known from the prior art.

The pharmacological action of medicinal substances of formula I is based on their interaction with muscarinic acetylcholine receptors (muscarine receptors). They are therefore referred to as m-cholinoceptor antagonists or parasympatholytics or—owing to their relaxing effect on smooth muscles—as neurotropic spasmolytics. The multifarious effects of the parasympatholytics include: acceleration of the heart rate, reduced secretion of tears, saliva, perspiration, and of the glands of the digestive tract, relaxation of the smooth muscles of the bronchi, the gastrointestinal tract, the bile ducts, the urethra and the urinary bladder, pupil dilation and impairment of accommodation. Quaternary spasmolytics, which include the compounds of the formula I, do not cross the blood-brain barrier and therefore have no central activity. Depending on the mode of administration, the desired and undesired effects of parasympatholytics vary. If these substances are used as spasmolytics, the reduced secretion of saliva or pupil dilation, for example, will be referred to as side effect.

Based on recent research, it is known that the structure of muscarine receptors is not uniform, but that the pharmacological effects can be attributed to interactions with at least four different muscarine-receptor subtypes. On the one hand, their distribution in different organs varies and, on the other hand, different muscarine receptor subtypes having different functions are involved in some neuronal signal transduction cascades. Various effects or side effects can be attributed to interactions with the different receptor subtypes, so that high subtype specificity is one of the aims in the development of modern spasmolytics.

Glycopyrronium bromide is an active compound which has been established for a long time but which does not meet the requirements of a “modern” therapeutic of this type.

However, glycopyrronium bromide is not only a racemate but additionally a mixture of diastereomers in which, depending on the preparation process, the ratios of the individual isomers in the product can in fact vary. Such isomeric active compound mixtures may therefore show random subtype profiles, making targeted use difficult and provoking the occurrence of undesirable side effects.

SUMMARY OF THE INVENTION

It is accordingly an object of the invention to provide enantiomerically pure esters, as well as processes for their preparation and their therapeutic use, that overcome the above-mentioned disadvantages of the prior art racemates of this type.

With the foregoing and other objects in view, the present invention provides enantiomerically pure esters enantiomerically enriched to an enantiomeric purity of 90% minimum enantiomeric excess (ee) selected from the group consisting of the (3R,2'R)—, (3S,2'R)—, (3R,2'S)— and (3S,2'S)-configured enantiomers of the formula I (II)

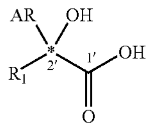

in which $R_1$ is a mono-, bi- or tricyclic, saturated or unsaturated $C_3$-$C_9$-cycloaliphatic radical which is unsubstituted or substituted by one or more $C_1$-$C_6$-alkyl, $C_2$-$C_6$-alkenyl and/or $C_2$-$C_6$-alkynyl radical(s) and/or by one or more of the halogen atoms fluorine, chlorine, bromine or iodine;

$R_2$ is a $C_1$-$C_6$-alkyl, $C_2$-$C_6$-alkenyl or $C_2$-$C_6$-alkynyl radical which is unsubstituted or substituted by one or more of the halogen atoms fluorine, chlorine, bromine or iodine;

$R_3$ is a $C_1$-$C_6$-alkyl, $C_2$-$C_6$-alkenyl or $C_2$-$C_6$-alkynyl radical which is unsubstituted or substituted by one or more of the halogen atoms fluorine, chlorine, bromine or iodine;

AR is an aromatic radical having 6 to 10 carbon atoms which can be substituted by one or more lower alkyl group(s) having 1 to 6 carbon atoms, trifluoromethyl group(s), cyano group(s), alkoxy group(s), nitrogroup(s), amino group(s) and/or one or more halogen atom(s)—identical to or different from one another or a 5- to 6-membered heteroaromatic ring containing oxygen, sulfur and/or nitrogen as heteroatoms and to which a further aromatic radical can be fused and which can be unsubstituted or substituted by one or more lower alkyl group(s) having 1 to 3 carbon atoms, trifluoromethyl group(s), cyano group(s), alkoxy group(s), nitro group(s), amino group(s)and/or one or more halogen atom(s)—identical to or different from one another;

n is an integer 1, 2 or 3; and

A is an anion of a pharmacologically acceptable acid.

In accordance with an additional feature of the invention, there are provided processes for the preparation of these enantiomerically pure esters of formula I and their use as medicaments.

In accordance with a further feature of the invention, preference is given to compounds of the formula I in which $R_1$ is a mono- or bicyclic $C_5$-$C_7$-cycloalkyl radical which is unsubstituted or substituted by one or more $C_1$-$C_3$-alkyl, $C_2$-$C_6$-alkenyl or $C_2$-$C_6$-alkynyl radical(s) and/or by one or more halogen atom(s) such as fluorine, chlorine, bromine or iodine;

$R_1$ is a mono- or bicyclic $C_5$-$C_7$-cycloaliphatic radical which is unsubstituted or substituted by one or more $C_1$-$C_3$-alkyl, $C_2$-$C_6$-alkenyl or $C_2$-$C_6$-alkynyl radical(s) and/or by one or more of the halogen atoms fluorine, chlorine, bromine or iodine;

$R_2$ is a $C_1$-$C_3$-alkyl, $C_2$-$C_4$-alkenyl or $C_2$-$C_4$-alkynyl radical which is unsubstituted or substituted by one or more halogen atoms fluorine, chlorine, bromine or iodine;

$R_3$ is a $C_1$-$C_3$-alkyl, $C_2$-$C_4$-alkenyl or $C_2$-$C_4$-alkynyl radical which is unsubstituted or substituted by one or more halogen atoms fluorine, chlorine, bromine or iodine;

AR is a $C_6$-$C_{10}$-aromatic radical or a heteroaromatic radical containing sulfur as heteroatom;

n is an integer 1 or 2; and

A is an anion of a pharmacologically acceptable mineral acid or of a carboxylic acid.

Special preference according to this invention is given to those enantiomerically pure esters of formula I in which $R_1$ is a cyclopentyl, a cyclohexyl or a norbornyl radical;

$R_2$ is a methyl radical;

$R_3$ is a methyl radical;

AR is a phenyl radical or thienyl radical;

n is an integer 1 or 2;

A is fluoride, chloride, bromide or iodide, and in which OH, AR and $R_1$ are arranged clockwise when viewed looking toward the carboxyl group.

In accordance with this invention, "enantiomerically pure" is defined in terms of "enantiomeric excess" (e.e.) which is calculated from the ratio of the difference between the amounts of the respective enantiomers present and the sum of these amounts (R−S)/(R+S) and expressed as a percentage. To illustrate, a preparation containing 95% of one enantiomer and 5% of the opposite enantiomer has an enantiomeric excess (e.e.) of (95−5)/(95+5)=90%. The enantiomerically pure esters of formula I according to this invention have an e.e. of at least 90%, preferably at least 96%. Enantiomerically pure esters of formula I according to this invention with an e.e. of at least 96% are especially preferred, and even greater preference among these is given to enantiomerically pure esters of formula I according to this invention with an e.e. of at least 97% and particularly with an e.e. of at least 98%.

DESCRIPTION OF THE PREFERRED EMBODIMENTS

Unless defined otherwise, in formula I $C_1$-$C_6$-alkyl is a branched or unbranched alkyl radical having 1 to 6 carbon atoms which can be unsubstituted or substituted by one or more halogen atoms. For the purpose of the present invention, $C_1$-$C_6$-alkyl radicals are, for example, methyl, ethyl, propyl, 1-methylethyl (isopropyl), butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethyl propyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethyl butyl, 1-ethylbutyl, 2-ethylbutyl, 1,1,2-trimethylpropyl, 1,2,2-trimethylpropyl, 1-ethyl-l-methylpropyl and 1-ethyl-2-methylpropyl.

Unless indicated otherwise, alkyl substituents containing 1 to 3 carbonatoms are preferably methyl, ethyl, n-propyl or isopropyl.

Unless defined otherwise, $C_2$-$C_6$-alkenyl is a branched or unbranched alkenyl radical having 2 to 6 carbon atoms which contains one or optionally two double bonds, and which may be unsubstituted or substituted by one or more halogen atoms. For the purpose of the present invention, $C_2$-$C_6$-alkenyl radicals are, for example vinyl, 2-propenyl (allyl), 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, among which the allyl radical is preferred.

Unless defined otherwise, $C_2$-$C_6$-alkynyl is a branched or unbranched alkynyl radical having 2 to 6 carbon atoms which may contain one or optionally two triple bonds or one triple bond and one double bond and which may be unsubstituted or substituted by one or more halogen atoms. For the purpose of the present invention, $C_2$-$C_6$-alkynyl radicals are, for example 2-propynyl (propargyl), 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 4-methyl-2-pentynyl, 1-methyl-3-pentynyl, 2-methyl-3-pentynyl, 1-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, among which the propargyl radical is preferred.

In general, cycloaliphatic radical is a saturated or unsaturated cyclic hydrocarbon radical having 3 to 9 carbon atoms which can be unsubstituted or substituted by a halogen atom or a plurality of halogen atoms—preferably fluorine—which can be identical to or different from one another. Preference is given to cyclic hydrocarbons having 5 or 6 carbon atoms. Examples which may be mentioned are cyclopropyl, cyclobutyl, cyclopentyl, cyclopentenyl, cyclohexyl, cyclohexenyl, cycloheptyl, cycloheptenyl, cycloheptadienyl, cyclooctyl, cyclooctenyl, cyclooctadienyl and cyclononynyl.

In general, aryl is an aromatic radical having 6 to 10 carbon atoms which can be unsubstituted or substituted by one or more lower alkyl group(s)having 1 to 3 carbon atoms, trifluoromethyl group(s), cyano group(s), alkoxy group(s), nitro group(s), amino group(s) and/or one or more halogen atom(s)—identical to or different from one another; the preferred aryl radical is an unsubstituted or substituted phenyl radical, preferred substituents being halogen—such as fluorine, chlorine or bromine-cyano and hydroxyl.

In the context of the definition given above, heteroaryl is generally a 5- to 6-membered ring which can contain oxygen, sulfur and/or nitrogen as heteroatoms and onto which another aromatic ring may be fused. Preference is given to 5- and 6-membered aromatic rings which contain an oxygen, a sulfur and/or up to two nitrogen atoms and which are optionally benzo-fused.

Particular heterocyclic systems which may be mentioned are, for example, acridinyl, acridonyl, alkylpyridinyl, anthraquinonyl, azazulenyl, azabenzanthracenyl, azabenzanthrenyl, azachrysenyl, azacyclazinyl, azaindolyl, azanaphthacenyl, azanaphthalenyl, azatriphenylenyl, azepinyl, azinoindolyl, azinopyrrolyl, benzacridinyl, benzazepinyl, benzofuryl, benzonaphthyridinyl, benzopyranonyl, benzopyranyl, benzopyronyl, benzoquinolinyl, benzoquinolizinyl, benzothiepinyl, benzothienyl, benzylisoquinolinyl, bipyridinyl, carbazolyl, carbolinyl, catechinyl, chromenopyronyl, chromonopyranyl, coumarinyl, coumaronyl, diazaanthracenyl, diazaphenanthrenyl, dibenzazepinyl, dibenzofuranyl, dibenzothienyl, dichromylenyl, dihydrofuranyl, dihydroisocoumarinyl, dihydroisoquinolinyl, dihydropyranyl, dihydropyridinyl, dihydropyridonyl, dihydropyronyl, dihydrothiopyranyl, dioxanthylenyl, flavanyl, flavonyl, fluoranyl, fluoresceinyl, furanochromanyl, furanonyl, furanoquinolinyl, furanyl, furopyranyl, furopyronyl, heteroazulenyl, hexahydropyrazinoisoquinolinyl, hydrofuranyl, hydrofuranonyl, hydroindolyl, hydropyranyl, hydropyridinyl, hydropyrrolyl, hydroquinolinyl, hydrothiocromenyl, hydrothienyl, indolizidinyl, indolizinyl, indolonyl, isatinyl, isatogenyl, isobenzofurandionyl, isobenzofuranyl, isochromanyl, isoflavonyl, isoindolinyl, isoindolobenzazepinyl, isoindolyl, isoquinolinyl, isoquinuclidinyl, monoazabenzonaphthenyl, naphthimidazopyridinedionyl, naphthindolizinedionyl, naptithodihydropyranyl, naphthofuranyl, naphthyridinyl, oxepinyl, oxindolyl, oxolenyl, perhydroindolyl, phenanthraquinonyl, phthalideisoquinolinyl, phthalimidyl, phthalonyl, pyrazinyl, pyranoazinyl, pyranoazolyl, pyranopyrandionyl, pyranopyridinyl, pyranoquinolinyl, pyranopyrazinyl, pyranyl, pyrazolopyridinyl, pyridinethionyl, pyridinonaphthalenyl, pyridinopyridinyl, pyridinyl, pyridocolinyl, pyridoindolyl, pyridopyridinyl, pyridopyrimidinyl, pyridopyrrolyl, pyridoquinolinyl, pyronyl, pyrrocolinyl, pyrrolizidinyl, pyrrolizinyl, pyrrolodioazinyl, pyrrolonyl, pyrrolopyrimidinyl, pyrroloquinolonyl, pyrrolyl, quinacridonyl, quinolinyl, quinolizidinyl, quinolizinyl, quinolonyl, quinuclidinyl, rhodaminyl, spirocoumaranyl, succinimidyl, sulfolanyl, sulfolenyl, tetrahydrofuranyl, tetrahydroisoquinoiinyl, tetrahydropyranyl, tetrahydropyridinyl, tetrahydrothiapyranyl, tetrahydrothienyl, tetrahydrothiopyranonyl, tetrahydrothiopyranyl, tetronyl, thiaphenyl, thiachromanyl, thianaphthenyl, thiapyranyl, thiapyronyl, thiazolopyridinyl, thienopyridinyl, thienopyrrolyl, thienothienyl, thiepinyl, thiochromenyl, thiocoumarinyl, thiopyranyl, triazaanthracenyl, triazinoindolyl, triazolopyridinyl, tropanyl, xanthenyl, xanthonyl, xanthydrolyl, alloxazinyl, anthranilyl, azabenzanthrenyl, azabenzonaphthenyl, azanaphthacenyl, azaphenoxazinyl, azapurinyl, azinyl, azoloazinyl, azolyl, benzazinyl, benzimidazolethionyl, benzimidazolonyl, benzisothiazolyl, benzisoxazolyl, benzocinnolinyl, benzodiazocinyl, benzodioxolanyl; benzodioxolyl, benzopyridazinyl, benzothiazepinyl, benzothiazinyl, benzothiazolyl, benzoxazinyl, bezoxazolinonyl, benzoxazolyl, cinnolinyl, depsidinyl, diazaphenanthrenyl, diazepinyl, diazinyl, dibenzoxazepinyl, dihydrobenzimidazolyl, dihydrobenzothiazinyl, dihydrooxazolyl, dihydropyridazinyl, dihydropyrimidinyl, dihydrothiazinyl, dioxenyl, dioxepinyl, dioxinonyl, dipyrimidopyrazinyl, dithiolenyl, dithiolyl, flavinyl, furopyrimidinyl, hexahydropyrazinoisoquinolinyl, hydroimidazolyl, hydropyrazinyl, hydropyrazolyl, hydropyridazinyl, hydropyrimidinyl, imidazolinyl, imidazolyl, imidazoquinazolinyl, imidazothiazolyl, indazolebenzopyrazolyl, indoxazenyl, inosinyl, isoalloxazinyl, isothiazolyl, isoxazolidinyl, isoxazolinonyl, isoxazolinyl, isoxazolonyl, isoxazolyl, lumazinyl, naphthimidazolyl, oroticyl, oxazinonyl, oxazolinonyl, oxazolinyl, oxazolonyl, oxazolopyrimidinyl, oxazolyl, perimidinyl, phenazinyl, phenothiazinyl, phenoxathiinyl, phenoxazinyl, phenoxazonyl, phthalazinyl, polyquinoxalinyl, pteridinyl, pterinyl, purinyl, pyrazinyl, pyrazolidinyl, pyrazolidonyl, pyrazolinonyl, pyrazolyl, pyridazinyl, pyridazonyl, pyridopyrazinyl, pyridopyrimidinyl, pyrimidinethionyl, pyrimidinyl, pyrimidionyl, pyrimidoazepinyl, pyrimidopteridinyl, pyrrolobenodiazepinyl, pyrrolodiazinyl, pyrrolopyrimidinyl, quinazolidinyl, quinazolinonyl, quinazolinyl, quinoxalinyl, tetrahydroquinoxalinyl, thiazepinyl, thiazinyl, thiazolidinonyl, thiazolidinyl, thiazolinonyl, thiazolinyl, thiazolobenzimidazolyl, thiazolyl, thienopyrimidinyl, thiazolidinonyl, triazolopyrimijdinyl, xanthinyl, azabenzonaphthenyl, benzofuroxanyl, benzothiadiazinyl, benzotriazepinonyl, benzotriazolyl, benzoxadiazinyl, dioxadiazinyl, dithiadazolyl, dithiazolyl, furazanyl, furoxanyl, hydrotriazolyl, hydroxytrizinyl, oxadiazinyl, oxadiazolyl, oxathiazinonyl, oxatriazolyl, pentazinyl, pentazolyl, petrazinyl, polyoxadiazolyl, sydonyl, tetraoxanyl, tetrazepinyl, tetrazinyl, tetrazolyl, thiadiazinyl, thiadiazolinyl, thiadiazolyl, thiadioxazinyl, thiatriazinyl, thiatriazolyl, triazepinyl, triazinoindolyl, triazinyl, triazolinedionyl, triazolinyl, triazolyl, triphenodioxazinyl, triphenodithiazinyl, or trithiadiazepinyl.

A pharmaceutically suitable salt is referred to as the salt of a pharmacologically acceptable acid, preferably a halogen acid.

The invention also provides a process for preparing compounds of formula I according to the invention in which a preferably tertiary aminoalcohol component in enantiomerically pure form and an arylcycloalkylhydroxycarbocylic acid in enantiomerically pure or preferably racemic form are reacted to give the ester which is finally quaternized using a suitable alkylating agent, preferably an alkyl halide. In the preferred process variant, after conversion of the racemic acid into the ester, the resulting diastereomers are separated by crystallization. The invention also provides the use of the enantiomerically pure esters of the formula I in medicaments.

The essential steps of the preparation process entail, in particular, that an enantiomerically pure a-hydroxycarboxylic acid (R or S enantiomer) of the formula II (II)

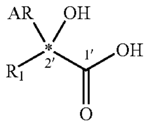

in which $R_1$ and AR are each as previously defined, or a lower alkyl ester or an activated acid derivative thereof, is reacted with the R or S enantiomer of an enantiomerically pure amino alcohol of the formula III (III)

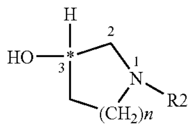

in which $R_2$ and n are each as previously defined, and the resulting enantiomerically pure ester of the formula IV (IV)

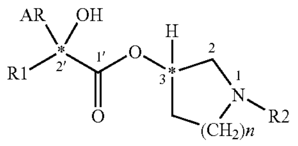

is reacted with an alkylating agent of the formula V $R_3$-X (V)

in which $R_3$ is as previously defined and X is a leaving group which can be replaced by a tertiary amino group, and the resulting salt is isolated or, if not a salt of pharmaceutically acceptable anion A, converted to such salt by anion exchange.

In an alternative process for preparing an enantiomerically pure ester of formula I, the racemic form of an α-a-hydroxycarboxylic acid of the formula II (II)

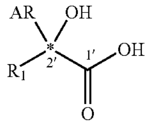

in which $R_1$ and AR are each as previously defined, or a lower alkyl ester or an activated acid derivative thereof, is reacted with the R or S enantiomer of an enantiomerically pure amino alcohol of the formula III (III)

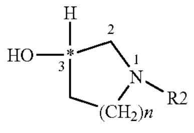

in which $R_2$ and n are each as previously defined, the resulting mixture of diastereomeric esters of the formula IV (IV)

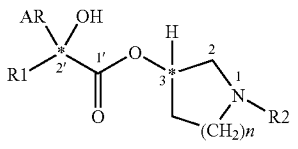

is separated, the desired diastereomer is reacted with an alkylating agent of the formula V $$R_3\text{-}X \qquad (V)$$

in which $R_3$ is as previously defined, and X is a leaving group which can be replaced by a tertiary amino group, and the resulting salt is isolated or, if not a salt of pharmaceutically acceptable anion A, converted to such salt by anion exchange.

When the racemate of a medicinal substance is separated into the enantiomers, it is frequently found that only one of the enantiomers is pharmacologically active. It can be seen from Example 9, especially from the logarithmically plotted graph in FIG. 1, that for compounds of the present patent application in principle all isomers can have affinity for the receptor. However, on the one hand, the individual enantiomers show distinctly different affinities and, on the other hand, there are also distinct variations in the $M_1$-$M_4$ subtype specificity, whereby the affinities differ by a factor of as much as approximately 1000. In particular, the high affinity for the $M_3$ receptor subtype, coupled with a relatively low affinity for the $M_2$ receptor subtype makes the preferred higher-affinity enantiomers (for example in Example 9:1b and 1c), particularly suitable active compounds for the therapy of spasms of the smooth muscles of the gastrointestinal tract and the urogenital tract and for the treatment of obstructive respiratory diseases. Owing to the fact that they can be administered at a particularly low dosage, because of their high affinity, and the fact that they have a particularly favorable subtype profile they afford therapeutic results more efficiently, and have a considerably reduced potential for side effects.

Another particularly important factor for the therapeutic use of enantiomers of the formula I consists in the kinetic subtype selectivity. As can be seen in Example 10 and FIG. 2, the dissociation half-times of the individual enantiomers 1a-1d of the compound of the formula I (AR=phenyl, $R_1$=cyclopentyl, $R_2$=$R_3$=methyl, n=1, A=1), for the $M_3$ receptor subtype are between 1 minute and 120 minutes, whereas the dissociation half-times on the $M_1$, $M_2$ and $M_4$ subtypes are in the range of a few minutes. In particular, compounds which have a particularly long dissociation half-time permit, owing to their strong affinity, a particularly low dosage, coupled with a long-lasting therapeutic effect. The possibility of influencing the duration of the pharmacological effect in a targeted manner by targeted selection of an enantiomer having a particular dissociation half-time represents a further important advance of the compounds of the present invention over the prior art. The properties described were unforseeable, and there were also no references in the literature.

To summarize, it can be stated that enantiomerically pure esters of formula I are distinguished from the prior art by their pharmacodynamic selectivity. In the preferred configuration, they have considerably higher affinity for is muscarenic $M_3$ receptors than for $M_2$ receptors, and in addition they show kinetic selectivity for $M_3$ receptors, i.e. they diffuse only very slowly from this receptor type. Owing to these distinctive properties, they are quite particularly suitable for the therapy of spasms of smooth muscles of the gastrointestinal tract and the urogenital tract, and for the treatment of obstructive respiratory diseases, such as bronchial asthma and chronic bronchitis. Compared with the nonselective parasympatholytics which have previously been used, they differ considerably in their pharmacological properties, owing to their defined subtype selectivity. Compared with known mixtures of stereoisomers or racemates, the compounds can additionally be employed at a particularly low dosage, thus minimizing side effects.

Accordingly, the invention prefers the use of enantiomerically pure esters(3R,2'R, 3S,2'R, 3R,2'S or −3S,2'S enantiomers) of the formula I in medicaments for the therapy of spasms of the smooth muscles of the gastrointestinal tract and the urogenital tract and for the treatment of obstructive respiratory diseases (bronchial asthma, chronic bronchitis). Such medicaments comprise a pharmaceutically acceptable carrier and an effective amount of enantiomerically pure ester of formula I. Any convenient carrier can be used, but preference is given to dosage forms for oral or injectable administration.

Special preference is given to using enantiomers of the formula I having high $M_3$ subtype selectivity ($pK_i$ greater than 10) and long dissociation half-times on the $M_3$ receptor in medicaments for the treatment of obstructive respiratory diseases, preferably bronchial asthma and chronic bronchitis. Particularly preferred dosage forms for such medicaments include an inhalable dry powder formulation and an aerosol for inhalation by the person in need of treatment. Such dry powder formulation can be formulated, for example, with an inert solid diluent such as lactose. Particularly suitable grades of lactose for inhalation having controlled particle properties are commercially available. Such aerosol can be formulated, for example, with a propellant such as dichlorodifluoromethane, trichlorofluoromethane, 2H-heptafluoropropane, octafluorocyclobutane and combinations thereof, and can include minor amounts of acceptable surfactant such as lecithin to facilitate absorption in bronchial tissues.

The invention described above is now illustrated by the examples below. To the person skilled in the art, various other embodiments will become evident from the description provided. However, express reference is made to the fact that the examples and the description are intended only for illustration and do not constitute a limitation of the invention.

EXAMPLES

Example 1

Preparation of (3S,2'S)-3-[(cyclopentylhydroxyphenylacetyl)oxy]-1,1-dimethylpyrrolidinium iodide 1a (formula I, AR=phenyl, $R_1$=cyclopentyl, $R_2$=$R_3$=methyl, n=1, A=1)

A dry reaction apparatus is charged with 20 mmol of (3S)-1-methyl-3-pyrrolidinol and 24 mmol of methyl 2-cyclopentyl-2-hydroxyphenylacetate in 500 ml of n-heptane absolute. 200 ml of heptane are then distilled over and discharged via a water separator to remove all traces of moisture. After cooling, 2 mmol of NaH or NaOMe (10 mol %) are added, and the mixture is once more heated to the boil. The temperature is chosen such that the n-heptane distills over only slowly. Over a period of 5-6 h, the amount distilled off is continuously replaced from the dropping funnel until the hydroxy ester has been completely converted. The reaction mixture is subjected to aqueous work-up and extracted with ether, and the crude product is then dried over $Na_2SO_4$/$K_2CO_3$ 2:1. The drying agent is filtered off with suction and the filtrate is then precooled in an ice bath and, with ice-cooling, admixed with ethereal HCl/2-butanone until saturated. The product is initially obtained as an oil. Addition of 2-butanone or distillative removal of ether gives a clear solution which is cooled with ice, causing the hydrochloride of the mixture of diastereomers (3S,2'R/S)-3-[(cyclopentylhydroxyphenylacetyl)oxy]-1-methylpyrrolidine (formula IV, AR=phenyl, $R_1$=cyclopentyl, $R_2$=methyl, n=1) to crystallize. Yield 15.7 mmol. M.p. 176° C.

Preparation of the Hydrogen Tartrates: Separation of Diastereomers by Fractional Crystallization:

To prepare the hydrogen tartrates, 15 mmol of the hydrochloride described above and $NaHCO_3/K_2CO_3$ buffer, pH 10, are transferred into a separatory funnel, and the aqueous phase is extracted three times with 150 ml of diethyl ether each time. The combined ethereal phases are admixed with 100 ml of ethyl acetate and dried over $Na_2SO_4/K_2CO_3$ 2:1. The drying agent is filtered off with suction and the filtrate is reduced to a volume of approximately 100 ml using a rotary evaporator. The solution is heated to approximately 60° C. and admixed with a solution of 1.2 eq (18 mmol) of enantiomerically pure tartaric acid in ethyl acetate. The hydrogen tartrate crystallizes overnight in a refrigerator. By repeated recrystallization, the diastereomers can be separated up to a de of 99%.

Yield 8.3 mmol of (3S,2'S)-3-[(cyclopentylhydroxy-phenylacetyl)oxy]-1-methylpyrrolidine, D-(−)-hydrogen tartrate formula IV (AR=phenyl, $R_1$=cyclopentyl, $R_2$=methyl, n=1); m.p. 178-179° C. $^1$H NMR spectrum (300 MHz $CD_4O$): δ(ppm) 1.3-1.7(M, 8H, cyclopentyl-$CH_2$), 2.05-2.1 (M, 1H, C4), 2.39-2.46 (M, 1H, C4), 2.77 (S, 3H, N-methyl), 2.97-3.0 (M, 1H, cyclopentyl C1), 3.18-3.25 (dd, 1H, C2, $^2$J=12.8 Hz, $^3$J=0-1 Hz), 3.31-3.5 (M, 2H, C5), 3.6-3.7 (dd, IH, $^3$J=5.2 Hz, $^2$J=13 Hz, C2), 4.42 (S, 2H, tartrate), 5.34-5.39(M, 1H, C3), 7.2-7.8 (M, 5H), assignments based on H,H COSY NMR Quaternization:

After liberating the bases by extraction with ether from bicarbonate buffer pH 10 and drying over $Na_2SO_4/K_2CO_3$ 2:1, quaternization is carried out by addition of 3 eq (20 mmol) of methyl iodide, and the resulting crystalline product(3S,2'S)~3-[(cyclopentylhydroxyphenylacetyl)oxy]-1,1-dimethylpyrrolidinium iodide 1a (formula I, AR=phenyl, $R_1$=cyclopentyl, $R_2$=$R_3$=methyl, n=1, A=1) is filtered off with suction. (The diastereomeric excesses can be determined by HPLC methods on β-cyclodextrin and "Whelck" phases, or by evaluating NMR spectra of the hydrogen tartrates described above.)

(3S,2'S)-3-[(cyclopentylhydroxyphenylacetyl)oxy]-1,1-dimethylpyrrolidinium iodide (1a) formula I (AR=phenyl, $R_1$=cyclopentyl, $R_2$=$R_3$=methyl, n=1, A=1); m.p. 165° C. $^1$H NMR spectrum (300 MHz $CD_4O$): δ (ppm) (1.15-1.4 (M, 2H), 1.5-1.7 (M, 6H), cyclopentylmethylene), 2.2 (M, 1H, C4), 2.63 (M, 1H, C4), 2.9 (S, 3H, N-methyl), 2.93-2.99 (M, 1H, cyclopentyl methine), 3.1(S, 3H, N-methyl), 3.43-3.47 (dd, 1H, C2, $^2$J=14 Hz, $^3$J=0 Hz), 3.5-3.7 (M, 2H, C5), 3.75 (dd, 1H, C2, $^2$J=13.7 Hz, $^3$J=6.05 Hz), 5.38(M, 1H, C3), 7.15-7.4(M, 3H), 7.5-7.65 (M, 2H) $^{13}$C-NMR 52 MHz $CD_40$ δ(ppm) (24.4-25.4) (4t, cyclopentyl methylene), 28.5 (t, C4), 47.4 (t, cyclopentyl methine), 51.3 (q, N-methyl), 51.8 (q, N-methyl), 63.6 (t, C5), 68.9 (t, C2), 72.0 (d, C3), 78.4 (s, hydroxy ester C2), 124.5(d), 126.1 (d), 126.7 (d), 140.5 (s), 172.4 (s).

The diastereomeric purity (de) was determined by comparing the integrals of the N-methyl protons of the diastereomeric hydrogentartrates in $^1$H NMR spectra (300 MHz, $CD_40$), or by HPLC analysis on β-cyclodextrin phases. (Cyclobond β-CD—OH, 50*0.4 cm, buffer: 85% $H_20$, 15% $CH_3CN$, 0.2% $CH_3COOH$ V/V, 0.35 ml/min isocratic, UV detection: 236 nm).

Example 2

Preparation of (3S, 2'R)-3-[(cyclopentylhydroxyphenylacetyl)oxy]-1,1-dimethylpyrrolidinium iodide 1b (formula I, AR=phenyl, $R_1$=cyclopentyl, $R_2$=$R_3$=methyl, n=1, A=1)

From the mother liquors of the separation of diastereomers described in Example 1, the D-(−)-hydrogen tartrate of the (3S, 2'R)-configured compound is crystallized by addition of ether. Repeated recrystallization results in a de of >98%.

(3S,2'R)-3-[(cyclopentylhydroxyphenylacetyl)oxy]-1-methylpyrrolidine, D-(−)-hydrogen tartrate (formula IV, AR=phenyl, $R_1$=cyclopentyl, $R_2$=methyl, n=1): m.p. 158-160° C., $^1$H NMR (300 MHz $CD_40$): δ(ppm) 1.3-1.7 (M, 8H, cyclopentyl $CH_2$), 2.0-2.1(M, 1H, C4), 2.39-2.46 (M, 1H, C4), 2.81 S, 3H, N-methyl), 2.93-3.05 (M, 1H, cyclopentyl) C1), 3.24-3.4 (M, 3H, C2, C5), 3.63-3.7 (dd, 1H, $^3$J=5,2 Hz, $^2$J=13 Hz, C2), 4.42 (S, 2H, tartrate), 5.38 (M, 1H, C3), 7.2-7.7(M, 5H) Assignments based on H,H COSY NMR.

Quaternization was carried out as described above, giving the crystalline product (3S,2'R)-3-[(cyclopentylhydroxyphenylacetyl)oxy]-1,1-dimethylpyrrolidinium iodide 1b (formula I, AR=phenyl, $R_1$=cyclopentyl, $R_2$=$R_3$ methyl, n=1, A=1). M.p. 108-109° C. $^1$H NMR (300 MHz $CD_40$): δ (ppm) (1.15-1.4 (M, 2H), 1.5-1.7(M, 6H) cyclopentyl methylene), 2.2 (M, 1H, C4), 2.65-2.85 (M, 1H, C4), 3.01 (M, 1H, cyclopentyl methine, 3.06 (S, 3H, N-methyl), 3.1 (S, 3H, N-methyl), 3.55-3.8 (M, 3H, C2, C5), 4.07 (dd, 1H, C2, $^2$J=13.8 Hz, $^3$J=6.2 Hz), 5.48 (M, 1H, C3), 7.26-7.4 (M, 3H), 7.5-7.65 (M, 2H). $^{13}$C NMR (50 MHz $CD_40$)/DEPT and CH correlation): δ (ppm) (27.0 (t), 27.4 (t), 27.41 (t), 28.06 (t), cyclopentyl methylene), 31.26 (t, C4), 46.6 (t, cyclopentyl methine), 53.8 (q, N-methyl), 54.3 (q, N-methyl), 66.2 (t, C5), 71.5 (t, C2), 74.5 (d, C3), 81.2 (s, hydroxy ester C2), 127 (d), 128.8 (d), 129.35 (d), 143.2 (s), 175.0 (s).

The diastereomeric purity was determined as described in Example 1.

Example 3

Preparation of (3R,2'R)-3-[(cyclopentylhydroxyphenylacetyl)oxy]-1,1-dimethylpyrrolidinium iodide 1c (formula I, AR=phenyl, $R_1$=cyclopentul, $R_2$=$R_3$=methyl, n=1, A=1)

The preparation was carried out as described in Example 1, starting from (3R)-1-methyl-3-pyrrolidnol and using L(+) tartaric acid for separating the diastereomers. The process described in Example 1 gives (3R,2'R)-3-[(cyclopentylhydroxyphenylacetyl)oxy]-1,1-dimeththylpyrrolidinium iodide 1c (formula I, AR=phenyl, $R_1$=cyclopentyl, $R_2$=$R_3$=methyl, n=1, A=1). The [$^1$H] and [$^{13}$C] NMR analytical data correspond to those of the (3S,2'S)=-configured compound 1a given in Example 1. M.p. 165-166° C.

The diastereomeric purity was determined as described in Example 1.

Example 4

Preparation of (3R,2'S)-3-[(cyclopentylhydroxyphenylacetyl)oxy]-1,1-dimethylpyrrolidinium iodide 1d (formula I, AR=phenyl, $R_1$=cyclopentyl, $R_2$=$R_3$=methyl, N=1, A=1)

From the mother liquors of the separation of the diastereomers of the 3R-configured compounds described in Example 1, the L-(+)-hydrogen tartrate of the (3R,2'S)-configured compound is crystallized by addition of ether. Repeated recrystallization gives a de of >98%.

Quaternization is likewise carried out as described in Example 1, giving the crystalline product (3R,2'S)-3-[(cyclopentylhydroxyphenylacetyl)oxy]-1,1-dimethylpyrrolidinium iodide 1d (formula I, AR=phenyl, $R_1$=cyclopentyl, $R_2$=$R_3$=methyl, n=1, A=1). The [$^1$H] and [$^{13}$C] NMR analytical data correspond to those of the (3s,2'R)-configured compound 1b given in Example 2. M.p. 107-108° C.

The diasteromeric purity was determined as described in Example 1.

Formulae of the enantiomers 1a-1d of Examples 1-4 hydroxy ester C2'), 126.9 (d), 128.7 (d), 129.2 (d), 142.1 (s), 175.0 (s, tartrate carboxyl), 177.2 (s, hydroxy ester carboxyl).

For quaternization, the procedure given in Example 1 is modified in that methyl bromide in tert-butyl methyl ether is used.

(3S,2'S)-3-[(cyclohexylhydroxyphenylacetyl)oxy]-1,1-dimethylpyrrolidinium bromide 2a: 1H-NMR (300 MHz $CD_40$): δ (ppm) (1.1-2.0 (M, 1OH), cyclohexyl methylene), 2.1-2.3 (M, 1H, cHex methine), 2.35-2.45 (M, 1H, C4), 2.65-2.85 (M, 1H, C4), 3.07 (S, 3H, N-methyl), 3.21 (S, 3H, N-methyl), 3.55-3.8 (M, 3H, C2, C5), 3.85 (dd, 1H, C2, $^2J$=13.8 Hz, $^3J$=6.1 Hz), 5.47 (M, 1H, C3), 7.25-7.4 (M, 3H), 7.55-7.65 (M, 2H)

The diastereomeric purity (de) was determined by comparing the integrals of the N-methyl protons of the diastereomeric hydrogen tartrates at 2.78 ppm and 2.78 ppm in the $^1$H-NMR spectra (300 MHz, $CD_40$).

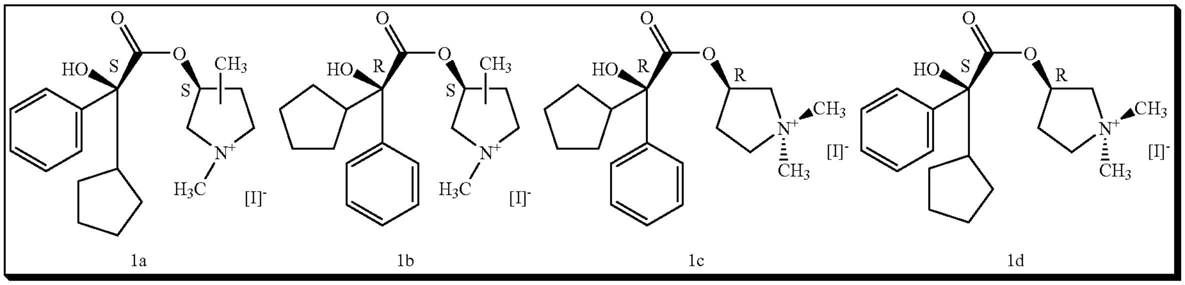

1a 1b 1c 1d

Example 5

Preparation of (3S,2'S)-3-[(cyclohexylhydroxyphenylacetyl)oxy]-1,1-dimethylpyrrolidinium bromide 2a (formula I, AR=phenyl, $R_1$ cyclohexyl, $R_2$=$R_3$=methyl, n=1, A=Br)

The compound of this Example 5 is prepared starting from (3S)-1-methyl-3-pyrrolidnol, methyl 2-cyclohexyl-2-hydroxyphenylacetate and NaOMe by the process described under Example 1. Transesterification and separation of the diastereomers of the 3S-configured L-(+)-hydrogen tartrates are carried out in a similar manner.

(3S,2'S)-3-[(cyclohexylhydroxyphenylacetyl)oxy]-1-methylpyrrolidine, L-(+)-hydrogen tartrate: formula IV, (AR=phenyl, $R_1$=cyclopentyl, $R_2$=methyl, n=1): $^1$H-NMR (300 MHz $CD_40$): δ (ppm)1.12-1.2 (M, 4H, cyclohexyl-$CH_2$), 1.2-1.64 (M, 3H, cyclohexyl-$CH_2$), 1.64-1.67 (M, 2H, cyclohexyl-$CH_2$), 1.75-1.85 (M, 1H, cyclohexyl-$CH_2$), 2.03-2.1 (M, 1H, C4), 2.25-2.4 (M, 1H, cyclohexylmethine), 2.40-2.55 (M, 1H, C4), 2.78 (S, 3H, N-methyl), 3.22 (dd, 1H, C2, $^2J$=13.3 Hz, $^3J$=0-1 Hz), 3.27-3.51 (M, 2H, C5), 3.65 (dd, 1H, 3J=5.42 Hz, $^2J$=13,2 Hz, C2), 4.42(S, 2H, tartrate), 5.37 (M, 1H, C3), 7.2-7.61 (M, 5H). The assignment was based on H,HCOSY NMR spectra. $^{13}$C-NMR (50 MHz $CD_40$/DEPT): δ (ppm) (26.71 (t), 27.35 (t), 27.47 (t), 28.71 (t), cyclohexyl methylene), 31.8 (t, C4), 42.5 (q, N-methyl), 46.92 (d, cyclohexyl methine), 55.35 (t, C5), 61.24 (t, C2), 74.2 (d, tartrate methine), 75.29d, C3), 82.7 (s, Example 6

Preparation of (3S,2'R)-3-[(cyclohexylhydroxyphenylacetyl)oxy]-1,1-dimethylpyrrolidinium bromide 2b (formula I, AR:=phenyl, $R_1$=cyclohexyl, $R_2$=$R_3$=methyl, n=1, A=Br)

From the mother liquors of the separation of the diastereomers for preparing (3S,2'S)-3-[(cyclohexylhydroxyphenylacetyl)oxy]-1,1-dimethylpyrrolidinium bromide (Example 5), the tertiary amino ester is liberated, after which the diastereomeric compound (3S,2'R)-3-[(cyclohexylhydroxyphenylacetyl)oxy]-1-methylpyrrolidine, D(−)-hydrogen tartrate, is crystallized.

(3S,2'R)-3-[(Cyclohexylhydroxyphenylacetyl)oxy]-1-methylpyrrolidine, D(−)-hydrogen tartrate:

$^1$H-NMR (300 MHz $CD_40$): δ(ppm) 1.12-1.2 (M, 4H, cyclohexyl $CH_2$), 1.2-1.64 (M, 3H, cyclohexyl $CH_2$), 1.64-1.67 (M, 2H, cyclohexyl $CH_2$), 1.75-1-85 (M, 1H, cyclohexyl $CH_2$), 2.03-2.08 (M, 1H, C4), 2.25-2.4(M, 1H, cyclohexyl methine), 2.40-2.55 (M, 1H, C4), 2.82 (S, 3H, N methyl), 3.27-3.34 (M, 2H, C5, C2), 3.44 (M, 1H, C5), 3.73 (dd, 1H, $^3J$=5.4 Hz, $^2J$ 13.3 Hz, C2), 4,42 (S, 2H, tartrate), 5.37 (M, 1H, C3), 7.2-7.61 (M, 5H). Assignment based on H,H COSY-NMR. $^{13}$C NMR (62.5 MHz $CD_40$): δ(ppm) (25.31 (t), 26 (t), 26.1 (t), 27.32 (t), cyclohexyl methylene), 30.57 (t, C4), 41.1 (q, N-methyl), 45.6 (d, cyclohexyl methine), 53.93 (t, C5), 59.7 (t, C2), 72.8 (d, tartrate methine), 73.82 (d, C3), 81.3 (s, hydroxy ester C2'), 125.54 (d), 127.2(d), 127.8 (d), 140.85 (s), 173.64 (s, tartrate carboxyl), 175.8 (s, hydroxy ester carboxyl)

Quaternization using methyl bromide in tert-butyl methyl ether gives (3S,2'R)-3-[(cyclohexylhydroxyphenylacetyl) oxyl-1,1-dimethylpyrrolidinium bromide. $^1$H-NMR (300 MHz $CD_4O$): δ (ppm) (1.1-1.8 (M, 10H), cyclohexyl methylene), 2.2-2.4 (M, 2H, C4&cHex methine), 2.65-2.85(M, 1H, C4), 3.03 (S, 3H, N-methyl), 3.21 (S, 3H, N-methyl), 3.55-3.8 (M, 3H, C2, C5), 3.86 (dd, 1H, C2, $^2J$=13.8 Hz, $^3J$=6.1 Hz), 5.48 (M, 1H, C3), 7.25-7.4 (M, 3H), 7.57-7.65 (M, 2H).

The diastereomeric purity (de) was determined as described in Example 5.

Example 7

Preparation of (3R,2'R)-3-[(cyclohexylhydroxyphenylacetyl)oxy]-1,1-dimethylpyrrolidinium bromide 2c (formula I, AR=phenyl, $R_1$=cyclohexyl, $R_2$=$R_3$=methyl, n=1, A=Br)

The compound of this Example 7 is prepared starting from(3R)-1-methyl-3-pyrrolidinol, methyl 2-cyclohexyl-2-hydroxyphenylacetate and NaOMe, using the process described in Example 1. Transesterification and separation of the diastereomers of the 3R-configured L-(+)-hydrogen tartrates is carried out in a similar manner. For quaternization, methyl bromide in tert-butyl methyl ether is employed, similar to the procedure given in Example 5. [1H] and [$^{13}$C]-NMR analysis identical to the (3S,2'S)-configured compound given in Example 5.

The diastereomeric purity (de) was determined as described in Example 5.

Example 8

Preparation of (3R,2'S)-3-[(cyclohexylhydroxyphenylacetyl)oxy]-1,1-dimethylpyrrolidinium bromide 2d (formula I, AR=phenyl, $R_1$=cyclohexyl, $R_2$ $R_3$=methyl, n=1, A=Br)

From the mother liquors of the separation of the diastereomers for preparing (3R,2'R)-3-[(cyclohexylhydroxyphenylacetyl)oxy]-1,1-dimethylpyrrolidium bromide (Example 7), the diastereomeric compound (3R,2'S)-3-[(cyclohexylhydroxyphenylacetyl)oxy]-1-methylpyrrolidine L-(+)-hydrogen tartrate, is crystallized. Quaternization using methylbromide in tert-butyl methyl ether gives (3R,2'S)-3-[(cyclohexylhydroxyphenylacetyl)oxy]-1,1-dimethylpyrrolidinium bromide. The [$^1$H]- and [$^{13}$C]-NMR analytical data correspond to those of the (3S,2'R)-configured compound detailed in Example 6.

The diastereomeric purity (de) was determined as described in Example 5.

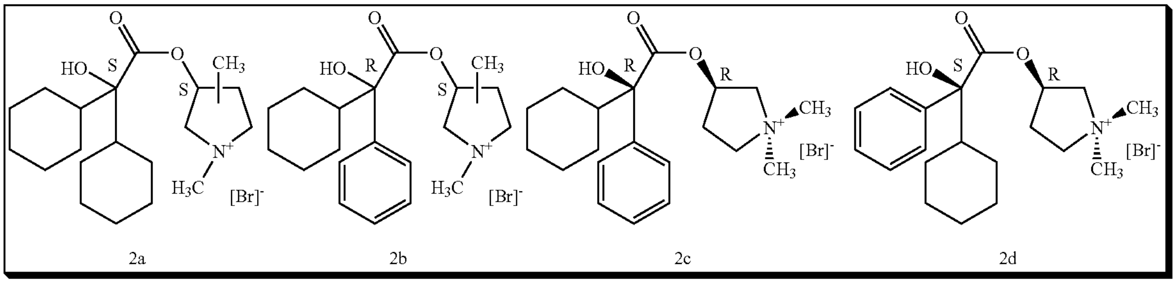

2a 2b 2c 2d

Formulae of the enantiomers 2a-2d of Examples 5-8

Example 9

Pharmacological Data of Compounds of the Structural Formula I Where AR=phenyl, $R_1$=Cyclopentyl, n=1, $R_2$=$R_3$=Methyl, A=Iodide

TAB 1

Pharmacological affinity data of the compounds 1a-1d

| Compound Abs. conf. §1 | $PA_2$ RVD (M1) | $pK_i$ M1 | $PA_2^a$ GPA (M2) | $pK_i^c$ M2 | $PEC_{50}^a$ GPI (M3) | $pK_i^b$ M3 | $pH_i^b$ M4 |
|---|---|---|---|---|---|---|---|
| (3S,2'S) Ia | 8.22 | 8.36 | 7.92 | 7.88 | 6.82 | 7.82. | 7.82 |
| 93S,2'R) Ib | 10.40 | 10.48 | 9.39 | 9.74 | 9.39 | 10.50 | 10.30 |
| (3R,2'R) Ic | 10.30 | 10.18 | 9.43 | 9.63 | 8.76 | 10.2 | 10.27 |
| (3R,2'S) Id | 9.53 | 9.36 | 8.69 | 9.00 | 8.57 | 9.63 | 9.40 |

[a]$pA_2$ and $pEC_{50}$ values from functional experiments on rabbit vas deferens, guinea pig atrium and guinea pig ileum.
[b]$pK_i$ values from [$^3$H]-,NMR binding studies on human $M_1$, $M_3$, $M_4$ receptors from CHO-Kl cells
[c]$pK_i$ values from [$^3$H]-NMS binding studies on $M_2$ receptors from preparations of rat hearts
[d]$pA_2$ = 7.61.

Table 1 thus shows the $pK_i$ values from [$^3$H] -NMR binding studies.

Example 10

Kinetic Data on the $M_3$ Receptor Subtype of Compounds of the Structural Formula I Where AR=Phenyl, $R_1$=Cyclopentyl, $R_2$=$R_3$=Methyl, n=1, A=Iodide

TAB 2

Association and dissociation constants, dissociation half-times on the $M_3$ receptor subtype

| Comp. ME-X[1] | k on[e] | k off[f] | $^t{}_{1/2}$[min][g] |
|---|---|---|---|
| (3S,2'S) Ia | 0.052 | 0.8000 | 1 |
| (3S,2'R) Ib | 0.410 | 0.0100 | 70 |
| (3R,2'R) Ic | 0.160 | 0.0060 | 120 |
| (3R,2'S) Id | 0.028 | 0.0080 | 90 |

[e]Association constant nmol/min,
[f]Dissociation constant nmol/min,
[g]Dissociation half-time in minutes.

Kinetic data from NMR binding studies on $M_3$ receptor subtypes from CHO-K1 cell lines.

1 The absolute configuration in the 2 position of the hydroxy acids was assigned by comparing the CD spectra with the corresponding cyclohexylmandelic acids. The absolute configuration of the 2-cyclohexyl-2-hydroxyphenyl acetic acids was assigned using the optical rotations in accordance with T. D. Inch et al., J. Chem. Soc. 1968, pp. 1693-1699.

Example 11a

Preparation of an inhalable powder formulation affording a dose of 350 μg (3R,2'R)-3-[cyclopentylhydroxyphenylacetyl)oxy]-1,1-dimethylpyrrolidinium bromide per 12.0 mg Powder formulation 3.50 g (3R,2'R)-3-[cyclopentylhydroxyphenylacetyl)oxy]-1,1-dimethylpyrrolidinium bromide and 16.50 g PrismaLac 40 (alpha-Lactose monohydrate, Meggle) are premixed with a spatula and sieved through a 0.8 mm sieve. The sieved blend is filled in a 250 ml glass flask and mixed for 20 min using a Turbula blender T10 B (W. A. Bachofen A G Maschinenfabrik, Basel) at 35 rpm.

Thereafter the blend is sieved a second time through the 0.8 mm sieve. Finally 100 g Lactose is added followed by blending the mixture with the Turbula blender for 20 min.

Content uniformity test data are for example: 97.4%, rsd. (standard deviation) +/−3.3%, n=10/respirable dose: stage 3-5, 33.3%, Astra Draco MSLI Example 11b Preparation of an inhalable powder formulation affording a dose of 350 μg (3R,2'S)-3-[cyclopentylhydroxyphenylacetyl)oxy]-1,1-dimethylpyrrolidinium bromide per 12.0 mg Powder formulation 3.50 g (3R,2'S)-3-[cyclopentylhydroxyphenylacetyl)oxy]-1,1-dimethylpyrrolidinium bromide and 16.50 g PrismaLac 40 (alpha-Lactose monohydrate, Meggle) are premixed with a spatula and sieved through a 0.8 mm sieve. The sieved blend is filled in a 250 ml glass flask and mixed for 20 min using a Turbula blender T10 B (W. A. Bachofen A G Maschinenfabrik, Basel) at 35 rpm.

Thereafter the blend is sieved a second time through the 0.8 mm sieve. Finally 100 g Lactose is added followed by blending the mixture with the Turbula blender for 20 min.

Content uniformity test data are for example: 97.4%i rsd. (standard deviation) +/−3.3%, n=10/respirable dose: stage 3-5, 33.3%, Astra Draco MSLI Example 11c Preparation of an inhalable powder formulation affording a dose of 350 μg (3S,2'R)-3-[cyclopentylhydroxyphenylacetyl)oxy]-1,1-dimethylpyrrolidinium bromide per 12.0 mg Powder formulation 3.50 g (3S,2'R)-3-[cyclopentylhydroxyphenylacetyl)oxy]-1,1-dimethylpyrrolidinium bromide and 16.50 g PrismaLac 40 (alpha-Lactose monohydrate, Meggle) are premixed with a spatula and sieved through a 0.8 mm sieve. The sieved blend is filled in a 250 ml glass flask and mixed for 20 min using a Turbula blender T10 B (W. A. Bachofen A G Maschinenfabrik, Basel) at 35 rpm.

Thereafter the blend is sieved a second time through the 0.8 mm sieve. Finally 100 g Lactose is added followed by blending the mixture with the Turbula blender for 20 min.

Content uniformity test data are for example: 97.4%, rsd. (standard deviation) +/−3.3%, n=10/respirable dose: stage 3-5, 33.3%, Astra Draco MSLI Example 11d Preparation of an inhalable powder formulation affording a dose of 350 μg (3S,2'S)-3-[cyclopentylhydroxyphenylacetyl)oxy]-1,1-dimethylpyrrolidinium bromide per 12.0 mg Powder formulation 3.50 g (3S,2'S)-3-[cyclopentylhydroxyphenylacetyl)oxy]-1,1-dimethylpyrrolidinium bromide and 16.50 g PrismaLac 40 (alpha-Lactose monohydrate, Meggle) are premixed with a spatula and sieved through a 0.8 mm sieve. The sieved blend is filled in a 250 ml glass flask and mixed for 20 min using a Turbula blender T10 B (W. A. Bachofen A G Maschinenfabrik, Basel) at 35 rpm.

Thereafter the blend is sieved a second time through the 0.8 mm sieve. Finally 100 g Lactose is added followed by blending the mixture with the Turbula blender for 20 min.

Content uniformity test data are for example: 97.4%, rsd. (standard deviation) +/−3.3%, n=10/respirable dose: stage 3-5, 33.3%, Astra Draco MSLI Example 12a Preparation of an inhalable powder formulation affording a dose of 350 μg (3R,2'R)-3-[cyclopentylhydroxyphenylacetyl)oxy]-1,1-dimethylpyrrolidinium bromide per 11.65 mg Powder formulation 0.825 g Pharmatose 450 M (alpha-Lactose monohydrate, DMV) and 32.18 g CapsuLac 60 (alpha-Lactose monohydrate, Meggle) is premixed with a spatula and sieved through a 0.3 mm sieve. The resulting blend is filled in a 100 ml glass flask and then blended with the Turbula blender T10 B for 60 min. 7.00 g (3R,2'R)-3-[cyclopentylhydroxyphe nylacetyl)oxy]-1,1-dimethlpyrrolidinium bromide and the 33.0 g Lactose blend is premixed with a spatula for 2 min and sieved through a 0.3 mm sieve. The sieved blend is filled in a 500 ml glass flask and mixed for 30 min using the Turbula blender. After adding 200 g CapsuLac 60 the blend is blended a second time with the Turbula blender for 10 min.

Content uniformity test data are for example: 99.8%, rsd. +/−3.2%, n=10

Example 12b

Preparation of an inhalable powder formulation affording a dose of 350 μg (3R,2'S)-3-[cyclopentyl-hydroxyphenylacetyl)oxy]-1,1-dimethylpyrrolidinium bromide per 11.65 mg Powder formulation 0.825 g Pharmatose 450 M (alpha-Lactose monohydrate, DMV) and 32.18 g CapsuLac 60 (alpha-Lactose monohydrate, Meggle) is premixed with a spatula and sieved through a 0.3 mm sieve. The resulting blend is filled in a 100 ml glass flask and then blended with the Turbula blender T10 B for 60 min. 7.00 g (3R,2'S)-3-[cyclopentylhydroxyphenylacetyl)oxy]-1,1-dimethlpyrrolidinium bromide and the 33.0 g Lactose blend is premixed with a spatula for 2 min and sieved through a 0.3 mm sieve. The sieved blend is filled in a 500 ml glass flask and mixed for 30 min using the Turbula blender. After adding 200 g CapsuLac 60 the blend is blended a second time with the Turbula blender for 10 min.

Content uniformity test data are for example: 99.8%, rsd. +/−3.2%, n=10

Example 12c

Preparation of an inhalable powder formulation affording a dose of 350 μg (3S,2'R)-3-[cyclopentyl-hydroxyphenylacetyl)oxy]-1,1-dimethylpyrrolidinium bromide per 11.65 mg Powder formulation 0.825 g Pharmatose 450 M (alpha-Lactose monohydrate, DMV) and 32.18 g CapsuLac 60 (alpha-Lactose monohydrate, Meggle) is premixed with a spatula and sieved through a 0.3 mm sieve. The resulting blend is filled in a 100 ml glass flask and then blended with the Turtbula blender T10 B for 60 min. 7.00 g (3S,2'R)-3-[cyclopentylhydroxyphenylacetyl)oxy]-1,1-dimethlpyrrolidinium bromide and the 33.0 g Lactose blend is premixed with a spatula for 2 min and sieved through a 0.3 mm sieve. The sieved blend is filled in a 500 ml glass flask and mixed for 30 min using the Turbula blender. After adding 200 g CapsuLac 60 the blend is blended a second time with the Turbula blender for 10 min.

Content uniformity test data are for example: 99.8%, rsd. +/−3.2%, n=10

Example 12d

Preparation of an inhalable powder formulation affording a dose of 350 μg(3S,2'S)-3-[cyclopentyl-hydroxyphenylacetyl)oxy]-1,1-dimethylpyrrolidinium bromide per 11.65 mg Powder formulation 0.825 g Pharmatose 450 M (alpha-Lactose monohydrate, DMV) and 32.18 g CapsuLac 60 (alpha-Lactose monohydrate, Meggle) is premixed with a spatula and sieved through a 0.3 mm sieve. The resulting blend is filled in a 100 ml glass flask and then blended with the Turbula blender T10 B for 60 min. 7.00 g (3S,2'S)-3-[cyclopentylhydroxyphenylacetyl)oxy]-1,1-dimethlpyrrolidinium bromide and the 33.0 g Lactose blend is premixed with a spatula for 2 min and sieved through a 0.3 mm sieve. The sieved blend is filled in a 500 ml glass flask and mixed for 30 min using the Turbula blender. After adding 200 g CapsuLac 60 the blend is blended a second time with the Turbula blender for 10 min.

Content uniformity test data are for example: 99.8%, rsd. +/−3.2%, n=10

Example 13a

Preparation of an inhalable powder formulation affording a dose of 700 μg (3R,2'R)-3-[cyclopenty-hydroxyphenylacetyl)oxyl-1,1-dimethylpyrrolidinium bromide per 13.0 mg Powder formulation 14.0 g (3R,2'R)-3-[Cyclopentylhydroxyphenylacetyl) oxy]-1,1-dimethlpyrrolidinium Bromide and 46.0 g InhaLac 70 (alpha-Lactose monohydrate, Meggle) are premixed with a spatula and sieved through a 0.5 mm sieve. The sieved blend is filled in a 500 ml glass flask and mixed for 30 min using a Turbula blender. Finally 200 g Lactose is added followed by blending the mixture with the Turbula blender for 10 min.

Content uniformity test data are for example: 97.2%, rsd. +/−0.6%, n=10/respirable dose: stage 3-5, 50.9%, Astra Draco MSLI

Example 13b

Preparation of an inhalable powder formulation affording a dose of 700 μq (3R,2'S)-3-[cyclopenty-hydroxyphenylacetyl)oxy]-1,1-dimethylpyrrolidinium bromide per 13.0 mg Powder formulation 14.0 g (3R,2'S)-3-[cyclopentylhydroxyphenylacetyl) oxy]-1,1-dimethlpyrrolidinium bromide and 46.0 g InhaLac 70 (alpha-Lactose monohydrate, Meggle) are premixed with a spatula and sieved through a 0.5 mm sieve. The sieved blend is filled in a 500 ml glass flask and mixed for 30 min using a Turbula blender. Finally 200 g Lactose is added followed by blending the mixture with the Turbula blender for 10 min.

Content uniformity test data are for example: 97.2%, rsd. +/−0.6%, n=10/respirable dose: stage 3-5, 50.9%, Astra Draco MSLI

Example 13c

Preparation of an inhalable powder formulation affording a dose of 700 μq (3S,2'R)-3-[cyclopenty-hydroxyphenylacetyl)oxy]-1,1-dimethylpyrrolidinium bromide per 13.0 mg Powder formulation 14.0 g (3S,2'R)-3-[cyclopentylhydroxyphenylacetyl) oxy]-1,1-dimethlpyrrolidinium bromide and 46.0 g InhaLac 70 (alpha-Lactose monohydrate, Meggle) are premixed with a spatula and sieved through a 0.5 mm sieve. The sieved blend is filled in a 500 ml glass flask and mixed for 30 min using a Turbula blender. Finally 200 g Lactose is added followed by blending the mixture with the Turbula blender for 10 min.

Content uniformity test-data are for example: 97.2%, rsd. +/−0.6%, n=10/respirable dose: stage 3-5, 50.9%, Astra Draco MSLI Example 13d Preparation of an inhalable powder formulation affording a dose of 700 μg (3S,2'S)-3-[cyclopenty-hydroxyphenylacetyl)oxy]-1,1-dimethylpyrrolidinium bromide per 13.0 mg Powder formulation 14.0 g (3S,2'S)-3-[cyclopentylhydroxyphenylacetyl)oxy]-1,1-dimethlpyrrolidinium bromide and 46.0 g InhaLac 70 (alpha-Lactose monohydrate, Meggle) are premixed with a spatula and sieved through a 0.5 mm sieve. The sieved blend is filled in a 500 ml glass flask and mixed for 30 min using a Turbula blender. Finally 200 g Lactose is added followed by blending is the mixture with the Turbula blender for 10 min.

Content uniformity test data are for example: 97.2%, rsd. +/−0.6%, n=10/respirable dose: stage 3-5, 50.9%, Astra Draco MSLI Example 14a Preparation of an inhalable powder formulation affording a dose of 350 μg (3R,2'R)-3-[cyclohexyl-hydroxyphenylacetyl)oxy]-1,1-dimethylpyrrolidinium bromide per 12.0 mg Powder formulation 3.50 g (3R,2'R)-3-[cyclohexylhydroxyphenylacetyl)oxy]-1,1-dimethylpyrrplidinium bromide and 16.50 g PrismaLac 40 (alpha-Lactose monohydrate, Meggle) are premixed with a spatula and sieved through a 0.8 mm sieve. The sieved blend is filled in a 250 ml glass flask and mixed for 20 min using a Turbula blender T10 B (W. A. Bachofen A G Maschinenfabrik, Basel) at 35 rpm Thereafter the blend is sieved a second time through the 0.8 mm sieve. Finally 100 g Lactose is added followed by blending the mixture with the Turbula blender for 20 min.

Content uniformity test data are for example: 97.4%, rsd. +/−3.3%, n=10/respirable dose: stage 3-5, 33.3%, Astra Draco MSLI Example 14b Preparation of an inhalable powder formulation affording a dose of 350 μg 3R,2'S)-3-[cyclohexyl-hydroxyphenylacetyl)oxy]-1,1-dimethylpyrrolidinium bromide per 12.0 mg Powder formulation 3.50 g (3R,2'S)-3-[cyclohexylhydroxyphenylacetyl)oxy]-1,1-dimethylpyrrolidinium bromide and 16.50 g PrismaLac 40 (alpha-Lactose monohydrate, Meggle) are premixed with a spatula and sieved through a 0.8 mm sieve. The sieved blend is filled in a 250 ml glass flask and mixed for 20 min using a Turbula blender T10 B (W. A. Bachofen A G Maschinenfabrik, Basel) at 35 rpm Thereafter the blend is sieved a second time through the 0.8 mm sieve. Finally 100 g Lactose is added followed by blending the mixture with the Turbula blender for 20 min.

Content uniformity test data are for example: 97.4%, rsd. +/−3.3%, n=10/respirable dose: stage 3-5, 33.3%, Astra Draco MSLI Example 14c Preparation of an inhalable powder formulation affording a dose of 350 μg (3S 2'R)-3-[cyclohexyl-hydroxyphenylacetyl)oxy]-1,1-dimethylpyrrolidinium bromide per 12.0 mg Powder formulation 3.50 g (3S,2'R)-3-[cyclohexylhydroxyphenylacetyl)oxy]-1,1-dimethylpyrrolidinium bromide and 16.50 g PrismaLac 40 (alpha-Lactose monohydrate, Meggle) are premixed with a spatula and sieved through a 0.8 mm sieve. The sieved blend is filled in a 250 ml glass flask and mixed for 20 min using a Turbula blender T10 B (W. A. Bachofen A G Maschinenfabrik, Basel) at 35 rpm Thereafter the blend is sieved a second time through the 0.8 mm sieve. Finally 100 g Lactose is added followed by blending the mixture with the Turbula blender for 20 min.

Content uniformity test data are for example: 97.4%, rsd. +/−3.3%, n=10/respirable dose: stage 3-5, 33.3%, Astra Draco MSLI Example 14d Preparation of an inhalable powder formulation affording a dose of 350 μg (3S,2'S)-3-[cyclohexylhydroxyphenylacetyl) oxy]-1,1-dimethylpyrrolidinium bromide per 12.0 mg Powder formulation 3.50 g (3S,2'S)-3-[cyclohexylhydroxyphenylacetyl)oxy]-1,1-dimethylpyrrolidinium bromide and 16.50 g PrismaLac 40 (alpha-Lactose monohydrate, Meggle) are premixed with a spatula and sieved through a 0.8 mm sieve. The sieved blend is filled in a 250 ml glass flask and mixed for 20 min using a Turbula blender T10 B (W. A. Bachofen A G Maschinenfabrik, Basel) at 35 rpm Thereafter the blend is sieved a second time through the 0.8 mm sieve. Finally 100 g Lactose is added followed by blending the mixture with the Turbula blender for 20 min.

Content uniformity test data are for example: 97.4%, rsd. +/−3.3%, n=10/respirable dose: stage 3-5, 33.3%, Astra Draco MSLI Example 15a Preparation of an inhalable powder formulation affording a dose of 350 μg (3R,2'R)-3-[cyclohexyl-hydroxyphenylacetyl)oxy]-1,1-dimethylpyrrolidinium bromide per 11.65 mg Powder formulation 0.825 g Pharmatose 450 M (alpha-Lactose monohydrate, DMV) and 32.18 g CapsuLac 60 (alpha-Lactose monohydrate, Meggle) is premixed with a spatula and sieved through a 0.3 mm sieve. The resulting blend is filled in a 100 ml glass flask and then blended with the Turbula blender T10 B for 60 min. 7.00 g (3R,2'R)-3-[cyclohexylhydroxyphenylacetyl)oxy]-1,1-dimethylpyrrolidinium bromide and the 33.0 g Lactose blend is premixed with a spatula for 2 min and sieved through a 0.3 mm sieve. The sieved blend is filled in a 500 ml glass flask and mixed for 30 min using the Turbula blender. After adding 200 g CapsuLac 60 the blend is blended a second time with the Turbula blender for 10 min.

Content uniformity test data are for example: 99.8%, rsd. +/−3.2%, n=10

Example 15b

Preparation of an inhalable powder formulation affording a dose of 350 μg (3R,2'S)-3-[cyclohexyl-hydroxyphenylacetyl)oxy]-1,1-dimethylpyrrolidinium bromide per 11.65 mg Powder formulation 0.825 g Pharmatose 450 M (alpha-Lactose monohydrate, DMV) and 32.18 g CapsuLac 60 (alpha-Lactose monohydrate, Meggle) is premixed with a spatula and sieved through a 0.3 mm sieve. The resulting blend is filled in a 100 ml glass flask and then blended with the Turbula blender T10 B for 60 min.

7.00 g (3R,2'S)-3-[cyclohexylhydroxyphenylacetyl)oxy]-1,1-dimethylpyrrolidinium bromide and the 33.0 g Lactose blend is premixed with a spatula for 2 min and sieved through a 0.3 mm sieve. The sieved blend is filled in a 500 ml glass flask and mixed for 30 min using the Turbula blender. After adding 200 g CapsuLac 60 the blend is blended a second time with the Turbula blender for 10 min.

Content uniformity test data are for example: 99.8%, rsd. +/−3.2%, n=10

Example 15c

Preparation of an inhalable powder formulation affording a dose of 350 μg (3S,2'R)-3-[cyclohexyl-hydroxyphenylacetyl)oxy]-1,1-dimethylpyrrolidinium bromide per 11.65 mg Powder formulation 0.825 g Pharmatose 450 M (alpha-Lactose monohydrate, DMV) and 32.18 g CapsuLac 60 (alpha-Lactose monohydrate, Meggle) is premixed with a spatula and sieved through a 0.3 mm sieve.

The resulting blend is filled in a 100 ml glass flask and then blended with the Turbula blender T10 B for 60 min. 7.00 g (3S,2'R)-3-[cyclohexylhydroxyphenylacetyl)oxy]-1,1-dimethylpyrrolidinium bromide and the 33.0 g Lactose blend is premixed with a spatula for 2 min and sieved through a 0.3 mm sieve. The sieved blend is filled in a 500 ml glass flask and mixed for 30 min using the Turbula blender. After adding 200 g CapsuLac 60 the blend is blended a second time with the Turbula blender for 10 min.

Content uniformity test data are for example: 99.8%, rsd. +/−3.2%, n=10

Example 15d

Preparation of an inhalable powder formulation affording a dose of 350 μg (3S,2'S)-3-[cyclohexyl-hydroxyphenylacetyl)oxy]-1,1-dimethylpyrrolidinium bromide per 11.65 mg Powder formulation 0.825 g Pharmatose 450 M (alpha-Lactose monohydrate, DMV) and 32.18 g CapsuLac 60 (alpha-Lactose monohydrate, Meggle) is premixed with a spatula and sieved through a 0.3 mm sieve. The resulting blend is filled in a 100 ml glass flask and then blended with the Turbula blender T10 B for 60 min.

7.00 g (3S,2'S)-3-[cyclohexylhydroxyphenylacetyl)oxy]-1,1-dimethylpyrrolidinium bromide and the 33.0 g Lactose blend is premixed with a spatula for 2 min and sieved through a 0.3 mm sieve. The sieved blend is filled in a 500 ml glass flask and mixed for 30 min using the Turbula blender. After adding 200 g CapsuLac 60 the blend is blended a second time with the Turbula blender for 10 min.

Content uniformity test data are for example: 99.8%, rsd. +/−3.2%, n=10

Example 16a

Preparation of an inhalable powder formulation affording a dose of 700 μg (3R,2'R)-3-[cyclohexy-hydroxyphenylacetyl)oxy]-1,1-dimethylpyrrolidinium bromide per 13.0 mg Powder formulation 14.0 g (3R,2'R)-3-[cyclohexylhydroxyphenylacetyl)oxy]-1, 1-dimethypyrrolidinium bromide and 46.0 g InhaLac 70 (alpha-Lactose monohydrate, Meggle) are premixed with a spatula and sieved through a 0.5 mm sieve. The sieved blend is filled in a 500 ml glass flask and mixed for 30 min using a Turbula blender. Finally 200 g Lactose is added followed by blending the mixture with the Turbula blender for 10 min.

Content uniformity test data are for example, 97.2%, rsd. +/−0.6%, n=10/respirable dose: stage 3-5, 50.9%, Astra Draco MSLI Example 16b Preparation of an inhalable powder formulation affording a dose of 700 μg (3R,2'S)-3-[cyclohexy-hydroxyphenylacetyl)oxy]-1,1-dimethylpyrrolidinium bromide per 13.0 mg Powder formulation 14.0 g (3R,2'S)-3-[cyclohexylhydroxyphenylacetyl)oxy]-1,1-dimethypyrrolidinium bromide and 46.0 g InhaLac 70 (alpha-Lactose monohydrate, Meggle) are premixed with a spatula and sieved through a 0.5 mm sieve. The sieved blend is filled in a 500 ml glass flask and mixed for 30 min using a Turbula blender. Finally 200 g Lactose is added followed by blending the mixture with the Turbula blender for 10 min.

Content uniformity test data are for example, 97.2%, rsd. +/−0.6%, n=10/respirable dose: stage 3-5, 50.9%, Astra Draco MSLI Example 16c Preparation of an inhalable powder formulation affording a dose of 700 μg (3S,2'R)-3-[cyclohexy-hydroxyphenylacetyl)oxy]-1,1-dimethylpyrrolidinium bromide per 13.0 mg Powder formulation 14.0 g (3S,2'R)-3-[cyclohexylhydroxyphenylacetyl)oxy]-1,1-dimethypyrrolidinium bromide and 46.0 g InhaLac 70 (alpha-Lactose monohydrate, Meggle) are premixed with a spatula and sieved through a 0.5 mm sieve. The sieved blend is filled in a 500 ml glass flask and mixed for 30 min using a Turbula blender. Finally 200 g Lactose is added followed by blending the mixture with the Turbula blender for 10 min.

Content uniformity test data are for example, 97.2%, rsd. +/−0.6%, n=10/respirable dose: stage 3-5, 50.9%, Astra Draco MSLI Example 16d Preparation of an inhalable powder formulation affording a dose of 700 μg (3S,2'S)-3-[cyclohexy-hydroxyphenylacetyl)oxy]-1,1-dimethylpyrrolidinium bromide per 13.0 mg Powder formulation 14.0 g (3S,2'S)-3-[cyclohexylhydroxyphenylacetyl)oxy]-1,1-dimethypyrrolidinium bromide and 46.0 g InhaLac 70 (alpha-Lactose monohydrate, Meggle) are premixed with a spatula and sieved through a 0.5 mm sieve. The sieved blend is filled in a 500 ml glass flask and mixed for 30 min using a Turbula blender. Finally 200 g Lactose is added followed by blending the mixture with the Turbula blender for 10 min.

Content uniformity test data are for example, 97.2%, rsd. +/−0.6%, n=10/respirable dose: stage 3-5, 50.9%, Astra Draco MSLI Example 17

Preparation of an inhalable powder formulation affording a dose of 175 μg (3R,2'R)-3-[cyclopentyl-hydroxyphenylacetyl)oxy]-1,1-dimethylpyrrolidinium bromide per 12.0 mg Powder formulation 1.75 μg (3R,2'R)-3-[cyclopentylhydroxyphenylacetyl) oxy]-1,1-dimethylpyrrolidinium bromide and 16.50 g PrismaLac 40 (alpha-Lactose monohydrate, Meggle) are premixed with a spatula and sieved through a 0.8 m sieve. The sieved blend is filled in a 250 ml glass flask and mixed for 20 min using a Turbula blender T10 B (W. A. Bachofen A G Maschinenfabrik, Basel) at 35 rpm Thereafter the blend is sieved a second time through the 0.8 mm sieve. Finally 100 g lactose is added followed by blending the mixture with the turbula blender for 20 min. Content uniformity test data are for example: 97.4%, rsd. +/−3.3%, n=10/respirable dose: stage 3-5, 33.3%, Astra Draco MSLI Example 18

Preparation of an inhalable powder formulation affording a dose of 175 μg (3R,2'R)-3-[cyclopentyl-hydroxyphenylacetyl)oxy]-1,1-dimethylpyrrolidinium bromide per 11.65 mg Powder formulation 0.825 g Pharmatose 450 M (alpha-Lactose monohydrate, DMV) and 32.18 g CapsuLac 60 (alpha-Lactose monohydrate, Meggle) is premixed with a spatula and sieved through a 0.3 mm sieve. The resulting blend is filled in a 100 ml glass flask and then blended with the Turbula blender T10 B for 60 min.

3.50 g (3R,2 'R)-3-[cyclopentylhydroxyphenylacetyl) oxy]-1,1-dimethylpyrrolidinium bromide and the 33.0 g Lactose blend is premixed with a spatula for 2 min and sieved through a 0.3 mm sieve. The sieved blend is filled in a 500 ml glass flask and mixed for 30 min using the Turbula blender. After adding 200 g CapsuLac 60 the blend is blended a second time with the Turbula blender for 10 min.

Content uniformity test data are for example: 99.8%, rsd. +/−3.2%, n=10

Example 19

Preparation of an inhalable powder formulation affording a dose of 350 μg (3R,2'R)-3-[cyclopentyl-hydroxyphenylacetyl)oxy]-1,1-dimethylpyrrolidinium bromide per 13.0 mg Powder formulation 7.0 g (3R,2'R)-3-[cyclopentylhydroxyphenylacetyl)oxy]-1,1-dimethylpyrrolidinium bromide and 46.0 g InhaLac 70 (alpha-Lactose monohydrate, Meggle) are premixed with a spatula and sieved through a 0.5 mm sieve. The sieved blend is filled in a 500 ml glass flask and mixed for 30 min using a Turbula blender. Finally 200 g Lactose is added followed by blending the mixture with the Turbula blender for 10 min.

Content uniformity test data are for example: 97.2%, rsd. +/−0.6%. n=10/respirable dose: stage 3-5, 50.9%, Astra Dracoi MSLI Example 20

Preparation of an inhalable powder formulation affording a dose of 175 μg (3R,2'R)-3-[cyclohexyl-hydroxyphenylacetyl)oxy]-1,1-dimethylpyrrolidinium bromide per 12.0 mg Powder formulation 1.75 g (3R,2'R)-3-[cyclohexylhydroxyphenylacetyl)oxy]-1,1-dimethylpyrrolidinium bromide and 16.50 g PrismaLac 40 (alpha-Lactose monohydrate, Meggle) are premixed with a spatula and sieved through a 0.8 mm sieve. The sieved blend is filled in a 250 ml glass flask and mixed for 20 min using a Turbula blender T10 B (W. A. Bachofen A G Maschinenfabrik, Basel) at 35 rpm.

Thereafter the blend is sieved a second time through the 0.8 mm sieve. Finally 100 g Lactose is added followed by blending the mixture with the Turbula blender for 20 min.

Content uniformity test data are for example: 97.4%, rsd. +/−3.3%, n=10/respirable dose: stage 3-5, 33.3 %, Astra Draco, MSLI Example 21

Preparation of an inhalable powder formulation affording a dose of 175 μg (3R,2'R)-3-[cyclohexyl-hydroxyphenylacetyl)oxy]-1,1-dimethylpyrrolidinium bromide per 11.65 mg Powder formulation 0.825 g Pharmatose 450 M (alpha-Lactose monohydrate, DMV) and 32.18 g CapsuLac 60 (alpha-Lactose monohydrate, Meggle) is premixed with a spatula and sieved through a 0.3 mm sieve. The resulting blend is filled in a 100 ml glass flask and then blended with the Turbula blender T10 B for 60 min.

3.50 g (3R,2'R)-3-[cyclohexylhydroxyphenylacetyl)oxy]-1,1-dimethylpyrrolidinium bromide and the 33.0 g Lactose blend is premixed with a spatula for 2 min and sieved through a 0.3 mm sieve. The sieved blend is filled in a 500 ml glass flask and mixed for 30 min using the Turbula blender. After adding 200 g CapsuLac 60 the blend is blended a second time with the Turbula blender for 10 min.

Content uniformity test data are for example: 99.8%, rsd. +/−3.2%, n=10

Example 22

Preparation of an inhalable powder formulation affording a dose of 350 μg (3R,2'R)-3-[cyclohexyl-hydroxyphenylacetyl)oxy]-1,1-dimethylpyrrolidinium bromide/13.0 mg Powder formulation 7.0 g (3R,2'R)-3-[cyclohexylhydroxyphenylacetyl)oxy)]-1,1-dimethylpyrrolidinium bromide and 46.0 g InhaLac 70 (alpha-Lactose monohydrate, Meggle) are premixed with a spatula and sieved through a 0.5 mm sieve. The sieved blend is filled in a 500 ml glass flask and mixed for 30 min using a Turbula blender. Finally 200 g Lactose is added followed by blending the mixture with the Turbula blender for 10 min.

Content uniformity test data are for example: 97.2% rsd. +/−0.6%, n=10/respirable dose: stage 3-5, 50.9%, Astra Draco MSLI Example 23a Preparation of an aerosol formulation affording a dose of 350 μg (3R,2'R)3-[cyclopentylhydroxyphenylacetyl)oxy]-1,1-dimethylpyrrolidinium bromide per stroke (0.052 ml Suspension)

1000 g 2H-Heptafluoropropane (=HFA 227) are cooled to a temperature of about 55° C. and reacted with stirring with a solution of 10.32 g polyoxyethylene-25-glyceryl trioleate (trade name: Tagat$^R$ TO, Goldschmidt A G) in 10.32 g absolute ethanol. 5.16 g micronized (3R,2'R)-3-[cyclopentylhydroxyphenylacetyl)oxy]-1,1-dimethylpyrrolidinium bromid and 5.90 g peppermint oil are then added and the resultant suspension is intensively homogenized. With further stirring and cooling the suspension is made up to 1032 g with cooled propellant 227 and then filled into metal cans which are closed with dosage valves that release 52 μl of the suspension per stroke. Each stroke releases 350 μg (3R,2'R)- or (3R,2'S)- or (3S,2'R)- or (3S, 4'S)-3-[cyclopentylhydroxyphenylacetyl)oxy]-1,1-dimethylpyrrolidinium bromide.

Example 23b

Preparation of an aerosol formulation affording a dose of 350 μg (3R,2'S)-3-[cyclopentylhydroxyphenylacetyl)oxy]-1,1-dimethylpyrrolidinium bromide per stroke (0.052 ml Suspension)

1000 g 2H-Heptafluoropropane (=HFA 227) are cooled to a temperature of about minus 55° C. and reacted with stirring with a solution of 10.32 g polyoxyethylene-25-glyceryl trioleate (trade name: Tagat$^R$ TO, Goldschmidt A G) in 10.32 g absolute ethanol. 5.16 g micronized (3R,2S)-3-[cyclopentylhydroxyphenylacetyl)oxy]-1,1-dimethylpyrrolidinium bromide and 5.90 g peppermint oil are then added and the resultant suspension is intensively homogenized. With further stirring and cooling the suspension is made up to 1032 g with cooled propellant 227 and then filled into metal cans which are closed with dosage valves that release 52 μl of the suspension per stroke. Each stroke releases 350 μg (3R,2'R) 3-[cyclopentylhydroxyphenylacetyl)oxy]-1,1-dimethylpyrrolidinium bromide.

Example 23c

Preparation of an aerosol formulation affording a dose of 350 μg (3S,2'R)-3-[cyclopentylhydroxyphenylacetyl)oxy]-1,1-dimethylpyrrolidinium bromide per stroke (0.052 ml Suspension)

1000 g 2H-Heptafluoropropane (=HFA 227) are cooled to a temperature of about minus 55° C. and reacted with stirring with a solution of 10.32 g polyoxyethylene-25-glyceryl trioleate (trade name: Tagat$^R$ TO, Goldschmidt A G) in 10.32 g absolute ethanol. 5.16 g micronized (3S,2'R)-3-[cyclopentylhydroxyphenylacetyl)oxy]-1,1-dimethylpyrrolidinium bromid and 5.90 g peppermint oil are then added and the resultant suspension is intensively homogenized. With further stirring and cooling the suspension is made up to 1032 g with cooled propellant 227 and then filled into metal cans which are closed with dosage valves that release 52 μl of the suspension per stroke. Each stroke releases 350 μg (3S,2'R)-3-[cyclopentylhydroxyphenylacetyl)oxy]-1,1-dimethylpyrrolidinium bromide.

Example 23d

Preparation of an aerosol formulation affording a dose of 350 μg (3S,2'S)-3-[cyclopentylhydroxyphenylacetyl)oxy]-1,1-dimethylpyrrolidinium bromide per stroke (0.052 ml Suspension)

1000 g 2H-Heptafluoropropane (=HFA 227) are cooled to a temperature of about minus 55° C. and reacted with stirring with a solution of 10.32 g polyoxyethylene-25-glyceryl trioleate (trade name: Tagat$^R$ TO, Goldschmidt A G) in 10.32 g absolute ethanol. 5.16 g (3S,2'S)-3-[cyclopentylhydroxyphenylacetyl)oxy]-1,1-dimethylpyrrolidinium bromide and 5.90 g peppermint oil are then added and the resultant suspension is intensively homogenized. With further stirring and cooling the suspension is made up to 1032 g with cooled propellant 227 and then filled into metal cans which are closed with dosage valves that release 52 μl of the suspension per stroke. Each stroke releases 350 μg (3S, 4'S)-3-[cyclopentylhydroxyphenylacetyl)oxy]-1,1-dimethylpyrrolidinium bromide.

Example 24a

Preparation of an aerosol formulation affording a dose of 350 μg (3R,2'R)-3-[cyclohexylhydroxyphenylacetyl)oxy]-1,1-dimethylpyrrolidinium bromide per stroke (0.062 ml Suspension)

1000 g 2H-Heptafluoropropane (=HFA 227) are cooled to a temperature of about minus 55° C. and reacted with stirring with a solution of 10.32 g polyoxyethylene-25-glyceryl trioleate (trade name: Tagat$^R$ TO, Goldschmidt A G) in 10.32 g absolute ethanol. 5.16 g micronized (3R,2'R)3-[cyclohexylhydroxyphenylacetyl)oxy]-1,1-dimethylpyrrolidinium bromide and 5.90 g peppermint oil are then added and the resultant suspension is intensively homogenized. With further stirring and cooling the suspension is made up to 1032 g with cooled propellant 227 and then filled into metal cans which are closed with dosage valves that release 52 μl of the suspension per stroke. Each stroke releases 350 μg (3R,2'R)-3-[cyclohexylhydroxyphenylacetyl)oxy]-1,1-dimethylpyrrolidinium bromide.

Example 24b

Preparation of an aerosol formulation affording a dose of 350 μg (3R,2'S)-3-[cyclohexylhydroxyphenylacetyl)oxy]-1,1-dimethylpyrrolidinium bromide per stroke (0.062 ml Suspension)

1000 g 2H-Heptafluoropropane (=HFA 227) are cooled to a temperature of about minus 55° C. and reacted with stirring with a solution of 10.32 g polyoxyethylene-25-glyceryl trioleate (trade name: Tagat$^R$ TO, Goldschmidt A G) in 10.32 g absolute ethanol. 5.16 g micronized (3R,2'S)-3-[cyclohexylhydroxyphenylacetyl)oxy]-1,1-dimethylpyrrolidinium bromid and 5.90 q peppermint oil are then added and the resultant suspension is intensively homogenized. With further stirring and cooling the suspension is made up to 1032 g with cooled propellant 227 and then filled into metal cans which are closed with dosage valves that release 52 μl of the suspension per stroke. Each stroke releases 350 μg (3R,2'S)-3-[cyclohexylhydroxyphenylacetyl)oxy]-1,1-dimethylpyrrolidinium bromide.

Example 24c

Preparation of an aerosol formulation affording a dose of 350 µq (3S,2'R)-3-[cyclohexylhydroxyphenylacetyl)oxy]-1,1-dimethylpyrrolidinium bromide per stroke (0.062 ml Suspension)

1000 g 2H-Heptafluoropropane (=HFA 227) are cooled to a temperature of about minus 55° C. and reacted with stirring with a solution of 10.32 g polyoxyethylene-25-glyceryl trioleate (trade name: Tagat$^R$ TO, Goldschmidt A G) in 10.32 g absolute ethanol. 5.16 g micronized (3S,2'R)-3-[cyclohexylhydroxyphenylacetyl)oxy]-1,1-dimethylpyrrolidinium bromid and 5.90 g peppermint oil are then added and the resultant suspension is intensively homogenized. With further stirring and cooling the suspension is made up to 1032 g with cooled propellant 227 and then filled into metal cans which are closed with dosage valves that release 52 µl of the suspension per stroke. Each stroke releases 350 µg (3S,2'R)-3-[cyclohexylhydroxyphenylacetyl)oxy]-1,1-dimethylpyrrolidinium bromide.

Example 24d

Preparation of an aerosol formulation affording a dose of 350 µg (3S,2'S)-3-[cyclohexylhydroxyphenylacetyl)oxy]-1,1-dimethylpyrrolidinium bromide per stroke (0.062 ml Suspension)

1000 g 2H-Heptafluoropropane (=HFA 227) are cooled to a temperature of about minus 55° C. and reacted with stirring with a solution of 10.32 g polyoxyethylene-25-glyceryl trioleate (trade name: Tagat$^R$ TO, Goldschmidt A G) in 10.32 g absolute ethanol. 5.16 g micronized (3S,2'S)-3-[cyclohexylhydroxyphenylacetyl)oxy]-1,1-dimethylpyrrolidinium bromide and 5.90 g peppermint oil are then added and the resultant suspension is intensively homogenized. With further stirring and cooling the suspension is made up to 1032 g with cooled propellant 227 and then filled into metal cans which are closed with dosage valves that release 52 µl ofthe suspension per stroke. Each stroke releases 350µ (3S,2'S)-3-[cyclohexylhydroxyphenylacetyl)oxy]-1,1-dimethylpyrrolidinium bromide.

Example 25

Preparation of an aerosol formulation affording a dose of 175 µg (3R,2'R)-3-[cyclopentylhydroxyphenylacetyl)oxy]-1,1-dimethylpyrrolidinium bromide per stroke (0.052 ml Suspension)

1000 g 2H-Heptefluoropropane (=HFA 227) are cooled to a temperature of about minus 55° C. and-reacted with stirring with a solution of 10.32 g polyoxyethylene-25-glyceryl trioleate (trade name: Tagat$^R$ TO, Goldschmidt A G) in 10.32 g absolute ethanol. 2.58 g micronized (3R,2'R)-3-[cyclopentylhydroxyphenylacetyl)oxy]-1,1-dimethylpyrrolidinium bromid and 5.90 g peppermint oil are then added and the resultant suspension is intensively homogenized. With further stirring and cooling the suspension is made up to 1032 g with cooled propellant 227 and then filled into metal cans which are closed with dosage valves that release 52 µl of the suspension per stroke. Each stroke releases 175 µg (3R,2'R)-3-[cyclopentylhydroxyphenylacetyl)oxy]-1,1-dimethylpyrrolidinium bromide.

Example 26

Preparation of an aerosol formulation affording a dose of 175 µg (3R,2'R)-3-[cyclohexylhydrophenylacetyl)oxy]-1,1-dimethylpyrrolidinium bromide per stroke (0.052 ml suspension)

1000 g 2H-Heptafluoropropane (=HFA 227) are cooled to a temperature of about minus 55° C. and reacted with stirring with a solution of 10.32 g polyoxyethylene-25-glyceryl trioleate (trade name: Tagat$^R$ TO, Goldschmidt A G) in 10.32 g absolute ethanol. 2.58 g micronized (3R,2'R)-3-[cyclohexylhydroxyphenylacetyl)oxy]-1,1-dimethylpyrrolidinium bromid and 5.90 g peppermint oil are then added and the resultant suspension is intensively homogenized. With further stirring and cooling the suspension is made up to 1032 g with cooled propellant 227 and then filled into metal cans which are closed with dosage valves that release 52 µl of the suspension per stroke. Each stroke releases 175 µg (3R,2'R)-3-[cyclohexylhydroxyphenylacetyl)oxy]-1,1-dimethylpyrrolidinium bromide.

We claim:

1. A method of treatment of obstructive respiratory diseases by inhalative administration of a pharmaceutically suitable salt of the enantiomerically pure ester (3R,2'R)-3-[cyclohexylhydroxyphenylacetyl)oxy]-1,1-dimethylpyrrolidinium in an effective amount to a patient in need thereof.

2. The method according to claim 1, wherein the pharmaceutically suitable salt is selected from the group consisting of fluoride, chloride, bromide and iodide.

3. The method according to claim 1, wherein the (3R,2'R)-3-[cyclohexylhydroxyphenylacetyl)oxy]-1,1-dimethylpyrrolidinium has an enantiomeric purity of minimum 96% enantiomeric excess.

4. The method according to claim 1, wherein the (3R,2'R)-3-[cyclohexylhydroxyphenylacetyl)oxy]-1,1-dimethylpyrrolidinium has an enantiomeric purity of minimum 97% enantiomeric excess.

5. The method according to claim 1, wherein the (3R,2'R)-3-[cyclohexylhydroxyphenylacetyl)oxy]-1,1-dimethylpyrrolidinium has an enantiomeric purity of minimum 98% enantiomeric excess.

6. The method according to claim 1, wherein the (3R,2'R)-3-[cyclohexylhydroxyphenylacetyl)oxy]-1,1-dimethylpyrrolidinium salt is administered in the form of an aerosol formulation.

7. The method according to claim 1, wherein the (3R,2'R)-3-[cyclohexylhydroxyphenylacetyl)oxy]-1,1-dimethylpyrrolidinium salt is administered in the form of a dry powder formulation.

8. The method according to claim 1, wherein the obstructive respiratory disease is selected from the group consisting of bronchial asthma and chronic bronchitis.

9. The method according to claim 2, wherein the (3R,2'R)-3-[cyclohexylhydroxyphenylacetyl)oxy]-1,1-dimethylpyrrolidinium salt is administered in the form of an aerosol formulation.

10. The method according to claim 2, wherein the (3R,2'R)-3-[cyclohexylhydroxyphenylacetyl)oxy]-1,1-dimethylpyrrolidinium salt is administered in the form of a dry powder formulation.

11. The method according to claim 2, wherein the obstructive respiratory disease is selected from the group consisting of bronchial asthma and chronic bronchitis.

12. A method of treatment of obstructive respiratory diseases by inhalative administration of a pharmaceutically suitable salt of the enantiomerically pure ester (3S,2'R)-3-

[cyclohexylhydroxyphenylacetyl)oxy]-1,1-dimethylpyrrolidinium in an effective amount to a patient in need thereof.

13. The method according to claim 12, wherein the pharmaceutically suitable salt is selected from the group consisting of fluoride, chloride, bromide and iodide.

14. The method according to claim 12, wherein the (3S,2'R)-3-[cyclohexylhydroxyphenylacetyl)oxy]-1,1-dimethylpyrrolidinium has an enantiomeric purity of minimum 96% enantiomeric excess.

15. The method according to claim 12, wherein the (3S,2'R)-3-[cyclohexylhydroxyphenylacetyl)oxy]-1,1-dimethylpyrrolidinium has an enantiomeric purity of minimum 97% enantiomeric excess.

16. The method according to claim 12, wherein the (3S,2'R)-3-[cyclohexylhydroxyphenylacetyl)oxy]-1,1-dimethylpyrrolidinium has an enantiomeric purity of minimum 98% enantiomeric excess.

17. The method according to claim 12, wherein the (3S,2'R)-3-[cyclohexylhydroxyphenylacetyl)oxy]-1,1-dimethylpyrrolidinium salt is administered in the form of an aerosol formulation.

18. The method according to claim 12, wherein the (3S,2'R)-3-[cyclohexylhydroxyphenylacetyl)oxy]-1,1-dimethylpyrrolidinium salt is administered in the form of a dry powder formulation.

19. The method according to claim 12, wherein the obstructive respiratory disease is selected from the group consisting of bronchial asthma and chronic bronchitis.

20. The method according to claim 13, wherein the (3S,2'R)-3-[cyclohexylhydroxyphenylacetyl)oxy]-1,1-dimethylpyrrolidinium salt is administered in the form of an aerosol formulation.

21. The method according to claim 13, wherein the (3S,2'R)-3-[cyclohexylhydroxyphenylacetyl)oxy]-1,1-dimethylpyrrolidinium salt is administered in the form of a dry powder formulation.

22. The method according to claim 13, wherein the obstructive respiratory disease is selected from the group consisting of bronchial asthma and chronic bronchitis.

23. A method of treatment of spasms of smooth muscles by administration of a pharmaceutically suitable salt of an enantiomerically pure ester selected from the group consisting of (3R,2'R)-3-[cyclopentylhydroxyphenylacetyl)oxy]-1,1-dimethylpyrrolidinium, ((3S,2'R)-)-3-[cyclopentylhydroxyphenylacetyl)oxy]-1,1-dimethylpyrrolidinium, (3R,2'R)-3-[cyclohexylhydroxyphenylacetyl)oxy]-1,1-dimethylpyrrolidinium, and (3S,2'R)-3-[cyclohexylhydroxyphenylacetyl)oxy]-1,1-dimethylpyrrolidinium in an effective amount to a patient in need thereof.

24. The method according to claim 23, wherein the pharmaceutically suitable salt is selected from the group consisting of fluoride, chloride, bromide and iodide.

25. The method according to claim 23, wherein said ester has an enantiomeric purity of minimum 96% enantiomeric excess.

26. The method according to claim 23, wherein said ester has an enantiomeric purity of minimum 97% enantiomeric excess.

27. The method according to claim 23, wherein said ester has an enantiomeric purity of minimum 98% enantiomeric excess.

28. The method according to claim 23, wherein said ester is (3R,2'R)-3-[cyclopentylhydroxyphenylacetyl)oxy]-1,1-dimethylpyrrolidinium.

29. The method according to claim 23, wherein said ester is (3S,2'R)-3-[cyclopentylhydroxyphenylacetyl)oxy]-1,1-dimethylpyrrolidinium.

30. The method according to claim 23, wherein said ester is (3R,2'R)-3-[cyclohexylhydroxyphenylacetyl)Qxy]-1,1-dimethylpyrrolidinium.

31. The method according to claim 23, wherein said ester is (3S,2'R)-3-[cyclohexylhydroxyphenylacetyl)oxy]-1,1-dimethylpyrrolidinium.

32. The method according to claim 23, wherein said salt is administered by inhalation.

33. The method according to claim 23, wherein said salt is administered by inhalation of an aerosol formulation.

34. The method according to claim 23, wherein said salt is administered by inhalation of a dry powder formulation.

35. The method according to claim 24, wherein said salt is administered by inhalation of an aerosol formulation.

36. The method according to claim 24, wherein said salt is administered by inhalation of a dry powder formulation.

* * * * *